United States Patent [19]
Crawley et al.

[11] Patent Number: 5,134,148
[45] Date of Patent: Jul. 28, 1992

[54] HETEROCYCLES FOR USE AS INHIBITORS OF LEUKOTRIENES

[75] Inventors: Graham C. Crawley, Macclesfield; Philip N. Edwards, Bramhall, both of United Kingdom; Jean-Marc M. M. Girodeau, Rilly la Montagne, France

[73] Assignees: Imperial Chemical Industries PLC, London, England; ICI Pharma, Cedex, France

[21] Appl. No.: 758,491

[22] Filed: Sep. 5, 1991

Related U.S. Application Data

[63] Continuation of Ser. No. 485,875, Feb. 27, 1990, abandoned.

[30] Foreign Application Priority Data

Feb. 28, 1989 [EP] European Pat. Off. ........ 89400560.2
May 31, 1989 [EP] European Pat. Off. ........ 89401493.5

[51] Int. Cl.[5] .................... A61K 31/47; A61K 31/44; A61K 31/495; C07D 405/12

[52] U.S. Cl. .................................. 514/312; 546/157; 546/159; 546/172; 546/176; 546/177; 546/178; 546/179; 546/180; 546/256; 546/268; 546/275; 546/283; 546/284; 546/346; 546/149; 546/152; 546/153; 546/155; 549/416; 549/423; 514/249; 514/259; 514/307; 514/311; 514/313; 514/314; 514/336; 544/215; 544/235; 544/237; 544/238; 544/283; 544/284; 544/295; 544/296; 544/333; 544/335; 544/336; 544/353; 544/405

[58] Field of Search ............... 546/152, 153, 157, 155, 546/159, 172, 176-180; 514/311, 312, 314

[56] References Cited

U.S. PATENT DOCUMENTS

| 4,567,184 | 1/1986 | Musser et al. | 514/311 |
|---|---|---|---|
| 4,625,034 | 11/1986 | Neiss et al. | 546/152 |
| 4,631,287 | 12/1986 | Chakraborty et al. | 514/307 |
| 4,725,619 | 2/1988 | Chakraborty et al. | 514/443 |
| 4,728,668 | 3/1988 | Chakraborty et al. | 514/464 |
| 4,794,188 | 12/1988 | Musser et al. | 546/152 |
| 4,839,369 | 6/1989 | Youssefyeh et al. | 546/152 |
| 4,876,346 | 10/1989 | Musser et al. | 546/157 |
| 4,918,081 | 4/1990 | Huang | 514/311 |
| 4,920,130 | 4/1990 | Huang | 514/311 |
| 4,920,131 | 4/1990 | Huang | 514/311 |
| 4,920,132 | 4/1990 | Huang | 514/314 |
| 4,920,133 | 4/1990 | Huang | 514/314 |

FOREIGN PATENT DOCUMENTS

| 0110405 | 11/1983 | European Pat. Off. |
| 0181568 | 10/1985 | European Pat. Off. |
| 0190722 | 8/1986 | European Pat. Off. |
| 0200101 | 12/1986 | European Pat. Off. |
| 0271287 | 6/1988 | European Pat. Off. |
| 0349062 | 1/1990 | European Pat. Off. |

OTHER PUBLICATIONS

Journal of Medicinal Chemistry, vol. 30, No. 1, Jan. 1987, pp. 96-106.

Primary Examiner—Mukund J. Shah
Assistant Examiner—E. Bernhardt
Attorney, Agent, or Firm—Cushman, Darby & Cushman

[57] ABSTRACT

The invention concerns a heterocycle of the formula I

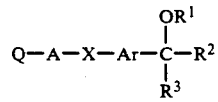

wherein
Q is an optionally substituted 6-membered monocyclic or 10-membered bicyclic heterocyclic moiety containing one or two nitrogen atoms;
A is (1-6C)alkylene, (3-6C)alkenylene, (3-6C)alkynylene or cyclo(3-6C)alkylene;
X is oxy, thio, sulphinyl, sulphonyl or imino;
Ar is phenylene which may optionally bear one or two substituents or Ar is an optionally substituted 6-membered heterocyclene moiety containing up to three nitrogen atoms;
$R^1$ is hydrogen, (1-6C)alkyl, (3-6C)alkenyl, (3-6C)alkynyl, cyano-(1-4C)alkyl or (2-4C)alkanoyl, or optionally substituted benzoyl;
and $R^2$ and $R^3$ together form a group of the formula —$A^2$—$X^2$—$A^3$— which, together with the carbon atom to which $A^2$ and $A^3$ are attached, defines a ring having 4 to 7 ring atoms, wherein $A^2$ and $A^3$, which may be the same or different, each is (1-4C)alkylene and $X^2$ is oxy, thio, sulphinyl, sulphonyl or imino; or a pharmaceutically-acceptable salt thereof.

The compounds of the invention are inhibitors of the enzyme 5-lipoxygenase.

15 Claims, No Drawings

HETEROCYCLES FOR USE AS INHIBITORS OF LEUKOTRIENES

This is a continuation of application Ser. No. 07/485,875, filed on Feb. 27, 1990, which was abandoned.

This invention concerns novel heterocycles and more particularly novel heterocycles which are inhibitors of the enzyme 5-lipoxygenase (hereinafter referred to as 5-LO). The invention also concerns processes for the manufacture of said heterocycles and novel pharmaceutical compositions containing said heterocycles. Also included in the invention is the use of said heterocycles in the treatment of various inflammatory and/or allergic diseases in which the direct or indirect products of 5-LO catalysed oxidation of arachidonic acid are involved, and the production of new medicaments for such use.

As stated above the heterocycles described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain heterocycles are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a heterocycle of the formula I (set out hereinafter) wherein Q is a 6-membered monocyclic or 10-membered bicyclic heterocyclic moiety containing one or two nitrogen atoms which may optionally bear one, two or three substituents selected from halogeno, hydroxy, oxo, carboxy, cyano, amino, (1–4C)alkyl, (1–4C)alkoxy, fluoro-(1–4C)alkyl, (1–4C)alkylamino, di-[(1–4C)alkyl]amino, hydroxy-(1–4C)alkyl, amino-(1–4C)alkyl, (1–4C)alkylamino-(1–4C)alkyl, di-[(1–4C)alkyl]amino-(1–4C)alkyl, amino-(2–4C)alkoxy, (1–4C)alkylamino-(2–4C)alkoxy, di-[(1–4C)alkyl]amino-(2–4C)alkoxy and phenyl-(1–4C)alkyl, and wherein the phenyl group in said phenyl-(1–4C)alkyl substituent may optionally bear a substituent selected from halogeno, (1–4C)alkyl and (1–4C)alkoxy;

wherein A is (1–6C)alkylene, (3–6C)alkenylene, (3–6C)alkynylene or cyclo(3–6C)alkylene;

wherein X is oxy, thio, sulphinyl, sulphonyl or imino;

wherein Ar is phenylene which may optionally bear one or two substituents selected from halogeno, hydroxy, amino, nitro, cyano, ureido, carbamoyl, (1–4C)alkyl, (3–4C)alkenyloxy, (1–4C)alkoxy, (1–4C)alkylthio, (1–4C)alkylsulphinyl, (1–4C)alkylsulphonyl, (1–4C)alkylamino, di-[(1–4C)alkyl]amino, fluoro-(1–4C)alkyl, (1–4C)alkoxycarbonyl, N-[(1–4C)alkyl]carbamoyl, N,N-di-[(1–4C)alkyl]carbamoyl, (2–4C)alkanoylamino, cyano-(1–4C)alkoxy, carbamoyl-(1–4C)alkoxy, amino-(2–4C)alkoxy, (1–4C)alkylamino-(2–4C)alkoxy, di-[(1–4C)alkyl]amino-(2–4C)alkoxy and (1–4C)alkoxycarbonyl-(1–4C)alkoxy; or Ar is a 6-membered heterocyclene moiety containing up to three nitrogen atoms which may optionally bear one or two substituents selected from halogeno, hydroxy, amino, cyano, (1–4C)alkyl, (1–4C)alkoxy, (1–4C)alkylamino and di-[(1–4C)alkyl]amino;

wherein $R^1$ is hydrogen, (1–6C)alkyl, (3–6C)alkenyl, (3–6C)alkynyl, cyano-(1–4C)alkyl or (2–4C)alkanoyl, or $R^1$ is benzoyl which may optionally bear a substituent selected from halogeno, (1–4C)alkyl and (1–4C)alkoxy; and wherein $R^2$ and $R^3$ together form a group of the formula $-A^2-X^2-A^3-$ which, together with the carbon atom to which $A^2$ and $A^3$ are attached, defines a ring having 4 to 7 ring atoms, wherein $A^2$ and $A^3$, which may be the same or different, each is (1–4C)alkylene and $X^2$ is oxy, thio, sulphinyl, sulphonyl or imino, and which ring may bear one or two substituents, which may be the same or different, selected from hydroxy, (1–4C)alkyl, (1–4C)alkoxy, (1–4C)alkylthio, (1–4C)alkylsulphinyl and (1–4C)alkylsulphonyl or which ring may bear a (1–4C)alkylenedioxy substituent;

or a pharmaceutically-acceptable salt thereof.

According to a further feature of the invention there is provided a heterocycle of the formula I wherein Q is a 6-membered monocyclic or 10-membered bicyclic heterocyclic moiety containing one or two nitrogen atoms which may optionally bear one or two substituents selected from halogeno, hydroxy, oxo, carboxy, cyano, amino, (1–4C)alkyl, (1–4C)alkoxy, fluoro-(1–4C)alkyl, (1–4C)alkylamino, di-[(1–4C)alkyl]amino, hydroxy-(1–4C)alkyl, amino-(1–4C)alkyl, (1–4C)alkylamino-(1–4C)alkyl, di-[(1–4C)alkyl]amino-(1–4C)alkyl, amino-(2–4C)alkoxy, (1–4C)alkylamino-(2–4C)alkoxy and di-[(1–4C)alkyl]amino-(2–4C)alkoxy;

wherein A is (1–6C)alkylene, (3–6C)alkenylene, (3–6C)alkynylene or cyclo(3–6C)alkylene;

wherein X is oxy, thio, sulphinyl, sulphonyl or imino;

wherein Ar is phenylene which may optionally bear one or two substituents selected from halogeno, hydroxy, amino, nitro, cyano, carbamoyl, (1–4C)alkyl, (3–4C)alkenyloxy, (1–4C)alkoxy, (1–4C)alkylthio, (1–4C)alkylsulphinyl, (1–4C)alkylsulphonyl, (1–4C)alkylamino, di-[(1–4C)alkyl]amino, fluoro-(1–4C)alkyl, (1–4C)alkoxycarbonyl, N-[(1–4C)alkyl]carbamoyl, N,N-di-[(1–4C)alkyl]carbamoyl, (2–4C)alkanoylamino, cyano-(1–4C)alkoxy, carbamoyl-(1–4C)alkoxy, amino-(2–4C)alkoxy, (1–4C)alkylamino-(2–4C)alkoxy, di-[(1–4C)alkyl]amino-(2–4C)alkoxy and (1–4C)alkoxycarbonyl-(1–4C)alkoxy; or Ar is a 6-membered heterocyclene moiety containing up to three nitrogen atoms which may optionally bear one or two substituents selected from halogeno, hydroxy, amino, cyano, (1–4C)alkyl, (1–4C)alkoxy, (1–4C)alkylamino and di-[(1–4C)alkyl]amino;

wherein $R^1$ is hydrogen, (1–6C)alkyl, (3–6C)alkenyl, (3–6C)alkynyl, cyano-(1–4C)alkyl or (2–4C)alkanoyl, or $R^1$ is benzoyl which may optionally bear a substituent selected from halogeno, (1–4C)alkyl and (1–4C)alkoxy; and wherein $R^2$ and $R^3$ together form a group of the formula —$A^2$—$X^2$—$A^3$— which, together with the carbon atom to which $A^2$ and $A^3$ are attached, defines a ring having 4 to 7 ring atoms, wherein $A^2$ and $A^3$, which may be the same or different, each is (1–4C)alkylene and $X^2$ is oxy, thio, sulphinyl, sulphonyl or imino, and which ring may bear one or two substituents, which may be the same or different, selected from hydroxy, (1–4C)alkyl, (1–4C)alkoxy, (1–4C)alkylthio, (1–4C)alkylsulphinyl and (1–4C)alkylsulphonyl or which ring may bear a (1–4C)alkylenedioxy substituent;

or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of formula I defined above may exist in optically active or racemic forms by virtue of one or more substituents containing an asymmetric carbon atom, the invention includes in its definition of active ingredient any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

It is also to be understood that, insofar as certain of the compounds of the formula I as defined above may exhibit the phenomenon of tautomerism, for example a compound of the formula I wherein Q bears an oxo or hydroxy substituent, and as any formula drawing presented herein may represent only one of the possible tautomeric forms the invention includes in its definition any tautomeric form of a compound of the formula I which possesses the property of inhibiting 5-LO and is not to be limited merely to any one tautomeric form utilised within the formulae drawings.

Suitable values for the generic terms referred to above include those set out below.

A suitable value for Q when it is a 6-membered monocyclic or 10-membered bicyclic heterocyclic moiety containing one or two nitrogen atoms is, for example, pyridyl, pyridazinyl, pyrimidinyl, pyrazinyl, quinolyl, isoquinolyl, cinnolinyl, quinazolinyl, quinoxalinyl, phthalazinyl or naphthyridinyl, or a hydrogenated derivative thereof such as for example, 1,2-dihydropyridyl or 1,2-dihydroquinolyl. The heterocyclic moiety may be attached through any available nitrogen atom and it may bear a substituent on any available position including on any available nitrogen atom.

When Q is a 10-membered bicyclic heterocyclic moiety containing one or two nitrogen atoms it will be appreciated that Q may be attached to A from either of the two rings of the bicyclic heterocyclic moiety.

Conveniently Q is, for example, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 2-quinolyl, 3-quinolyl, 5-quinolyl, 6-quinolyl, 7-quinolyl, 1-isoquinolyl, 3-isoquinolyl, 6-isoquinolyl, 7-isoquinolyl, 3-cinnolyl, 6-cinnolyl, 7-cinnolyl, 2-quinazolinyl, 4-quinazolinyl, 6-quinazolinyl, 7-quinazolinyl, 2-quinoxalinyl, 5-quinoxalinyl, 6-quinoxalinyl, 1-phthalazinyl, 6-phthalazinyl, 1,5-naphthyridin-2-yl, 1,5-naphthyridin-3-yl, 1,6-naphthyridin-3-yl, 1,6-naphthyridin-7-yl, 1,7-naphthyridin-3-yl, 1,7-naphthyridin-6-yl, 1,8-naphthyridin-3-yl, 2,6-naphthyridin-3-yl or 2,7-naphthyridin-3-yl.

A suitable value for a halogeno substituent which may be present on Q, Ar or $R^1$ is, for example, fluoro, chloro, bromo or iodo.

A suitable value for a (1–4C)alkyl substituent which may be present on Q, Ar or $R^1$ is, for example, methyl, ethyl, propyl, isopropyl, butyl, isobutyl or sec-butyl.

A suitable value for a (1–4C)alkoxy substituent which may be present on Q, Ar or $R^1$ is, for example, methoxy, ethoxy, propoxy, isopropoxy or butoxy.

A suitable value for a fluoro-(1–4C)alkyl substituent which may be present on Q or Ar, is, for example, fluoromethyl, difluoromethyl, trifluoromethyl, 2-fluoroethyl, 2,2,2-trifluoroethyl or pentafluoroethyl.

A suitable value for A when it is (1–6C)alkylene is, for example, methylene, ethylene, ethylidene, trimethylene, propylidene, tetramethylene or pentamethylene; when it is (3–6C)alkenylene is, for example, 1-propenylene, 2-methylprop-1-enylene, 3-methylprop-1-enylene, 1-butenylene or 2-butenylene; and when it is (3–6C)alkynylene is, for example, 1-propynylene, 3-methylprop-1-ynylene, 1-butynylene or 2-butynylene.

A suitable value for A when it is cyclo(3–6C)alkylene is, for example, cyclopropylidene, 1,2-cyclopropylene, cyclopentylidene, 1,2-cyclopentylene, cyclohexylidene or 1,4-cyclohexylene.

A suitable value for Ar when it is phenylene is, for example, 1,3-phenylene or 1,4-phenylene.

A suitable value for Ar when it is a 6-membered heterocyclene moiety containing up to three nitrogen atoms is, for example, pyridylene, pyrimidinylene, pyridazinylene, pyrazinylene or 1,3,5-triazinylene. Conveniently Ar when it is a 6-membered heterocyclene moiety containing up to three nitrogen atoms is, for example, 2,4-, 2,5-, 3,5- or 2,6-pyridylene, 2,4-, 2,5- or 4,6-pyrimidinylene, 3,5- or 3,6-pyridazinylene or 2,5- or 2,6-pyrazinylene.

Suitable values for substituents which may be present on Q or Ar include, for example:

| | |
|---|---|
| for (1–4C)alkylamino: | methylamino, ethylamino propylamino and butylamino; |
| for di-[(1–4C)alkyl]amino: | dimethylamino, diethylamino and dipropylamino; |
| for amino-(2–4C)alkoxy: | 2-aminoethoxy, 3-aminopropoxy and 4-aminobutoxy; |
| for (1–4C)alkylamino-(2–4C)-alkoxy: | 2-methylaminoethoxy, 3-methylaminopropoxy and 2-ethylaminoethoxy; |
| for di-[(1–4C)alkyl]amino-(2–4C)alkoxy: | 2-dimethylaminoethoxy, 3-dimethylaminopropoxy and 2-diethylaminoethoxy. |

Suitable values for substituents which may be present on Q include, for example:

| | |
|---|---|
| for hydroxy-(1–4C)alkyl: | hydroxymethyl, 1-hydroxyethyl, 2-hydroxyethyl, 2-hydroxypropyl and 3-hydroxypropyl; |
| for amino-(1–4C)alkyl: | aminomethyl, 1-aminoethyl, 2-aminoethyl, 2-aminopropyl and 3-aminopropyl; |
| for (1–4C)alkylamino-(1–4C)alkyl: | methylaminomethyl, 2-methylaminoethyl, 3-methylaminopropyl, ethylaminomethyl and 2-ethylaminoethyl; |
| for di-[(1–4C)alkyl]amino-(1–4C)alkyl: | dimethylaminomethyl, 2-dimethylaminoethyl, 3-dimethylaminopropyl, diethylaminomethyl and 2-diethylaminoethyl; |
| for phenyl-(1–4C)alkyl: | benzyl, phenethyl and 3-phenylpropyl. |

Suitable values for substituents which may be present on Ar include, for example:

| | |
|---|---|
| for (3–4C)alkenyloxy: | allyloxy, methylallyloxy, but-2-enyloxy and but-3-enyloxy; |
| for (1–4C)alkylthio: | methylthio, ethylthio, propylthio, isopropylthio and butylthio; |
| for (1–4C)alkylsulphinyl: | methylsulphinyl, ethylsulphinyl, propylsulphinyl, isopropylsulphinyl and butylsulphinyl; |
| for (1–4C)alkylsulphonyl: | methylsulphonyl, ethylsulphonyl, propylsulphonyl, isopropylsulphonyl and butylsulphonyl; |
| for (1–4C)alkoxycarbonyl: | methoxycarbonyl, ethoxycarbonyl and tert-butoxycarbonyl; |
| for N-[(1–4C)alkyl]carbamoyl: | N-methylcarbamoyl, N-ethylcarbamoyl and N-propylcarbamoyl; |
| for N,N-di-[(1–4C)alkyl]-carbamoyl: | N,N-dimethylcarbamoyl and N,N-diethylcarbamoyl; |
| for (2–4C)alkanoylamino: | acetamido, propionamido and butyramido; |
| for cyano-(1–4C)alkoxy: | cyanomethoxy, 2-cyanoethoxy and 3-cyanopropoxy; |
| for carbamoyl-(1–4C)alkoxy: | carbamoylmethoxy, 2-carbamoylethoxy and 3-carbamoylpropoxy; |
| for (1–4C)alkoxycarbonyl-(1–4C)alkoxy: | methoxycarbonylmethoxy, 2-methoxycarbonylethoxy, ethoxycarbonylmethoxy and 2-ethoxycarbonylethoxy. |

A suitable value for $R^1$ when it is (1–6C)alkyl is, for example, methyl, ethyl, propyl, butyl, pentyl or hexyl.

A suitable value for $R^1$ when it is (3–6C)alkenyl is, for example, allyl, 2-butenyl or 3-butenyl; and when it is (3–6C)alkynyl is, for example, 2-propynyl or 2-butynyl.

A suitable value for $R^1$ when it is (2–4C)alkanoyl is, for example, acetyl, propionyl or butyryl.

A suitable value for $R^1$ when it is cyano-(1–4C)alkyl is, for example, cyanomethyl, 2-cyanoethyl or 3-cyanopropyl.

When $R^2$ and $R^3$ together form a group of the formula —$A^2$—$X^2$—$A^3$— which, together with the carbon atom to which $A^2$ and $A^3$ are attached, defines a ring having 4 to 7 ring atoms then a suitable value for $A^2$ or $A^3$, which may be the same or different, when each is (1–4C)alkylene is, for example, methylene, ethylene, trimethylene or tetramethylene.

Suitable values for the one or two substituents which may be present on said 4- to 7-membered ring include for example:

| | |
|---|---|
| for (1–4C)alkyl: | methyl, ethyl, propyl, isopropyl and butyl; |
| for (1–4C)alkoxy: | methoxy, ethoxy, propoxy, isopropoxy and butoxy; |
| for (1–4C)alkylthio: | methylthio, ethylthio, propylthio, isopropylthio and butylthio; |
| for (1–4C)alkylsulphinyl: | methylsulphinyl, ethylsulphinyl, propylsulphinyl, isopropylsulphinyl and butylsulphinyl; |
| for (1–4C)alkylsulphonyl: | methylsulphonyl, ethylsulphonyl, propylsulphonyl, isopropylsulphonyl and butylsulphonyl; |
| for (1–4C)alkylenedioxy: | methylenedioxy and ethylenedioxy. |

A suitable pharmaceutically-acceptable salt of a heterocycle of the invention which is sufficiently basic is an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a heterocycle of the invention which is sufficiently acidic (for example a heterocycle of the invention which contains a carboxy group) is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, heterocycles of the formula I wherein:

(a) Q is 2-pyridyl, 3-pyridyl, 3-pyridazinyl, 2-pyrimidinyl or 2-pyrazinyl which may optionally bear one substituent selected from chloro, hydroxy, cyano, methyl, methoxy and trifluoromethyl; and A, X, Ar, $R^1$, $R^2$ and $R^3$ have any of the meanings defined hereinbefore;

(b) Q is 2-pyridyl, 3-pyridyl, 4-pyridyl, 2-pyrimidinyl or 2-pyrazinyl; A is 1-propenylene or 1-propynylene; and X is oxy; and Ar, $R^1$, $R^2$ and $R^3$ have any of the meanings defined hereinbefore;

(c) Q is 2-quinolyl, 3-quinolyl, 6-quinolyl, 7-quinolyl, 3-isoquinolyl, 6-isoquinolyl, 7-isoquinolyl, 3-cinnolyl, 2-quinazolinyl, 6-quinazolinyl, 2-quinoxalinyl, 6-quinoxalinyl, 6-phthalazinyl, 1,7-naphthyridin-3-yl, 1,7-naphthyridin-6-yl, 1,8-naphthyridin-3-yl or 2,7-naphthyridin-3-yl which may optionally bear one or two substituents selected from fluoro, chloro, hydroxy, oxo, cyano, methyl, methoxy and trifluoromethyl; and A, X, Ar, $R^1$, $R^2$ and $R^3$ have any of the meanings defined hereinbefore;

(d) Q is 3-quinolyl, 5-quinolyl, 6-quinolyl, 7-quinolyl, 1-isoquinolyl, 3-isoquinolyl, 2-quinazolinyl, 6-quinazolinyl or 6-quinoxalinyl which may optionally bear one, two or three substituents selected from fluoro, chloro, hydroxy, oxo, methyl, ethyl, propyl, trifluoromethyl, 2-fluoroethyl, 2-dimethylaminoethyl and benzyl; and A, X, Ar, $R^1$, $R^2$ and $R^3$ have any of the meanings defined hereinbefore;

(e) Q is 1,2-dihydro-2-oxoquinolin-3-yl, 1,2-dihydro-2-oxoquinolin-6-yl, 1,2-dihydro-2-oxoquinolin-7-yl, 3,4-dihydro-4-oxoquinazolin-6-yl, 1,2-dihydro-2-oxo-1,7- naphthyridin-3-yl or 1,2-dihydro-2-oxo-1,8-naphthyridin-3-yl which may optionally bear one or two substituents selected from fluoro, chloro, cyano, methyl, methoxy and trifluoromethyl; and A, X, Ar, $R^1$, $R^2$ and $R^3$ have any of the meanings defined hereinbefore;

(f) Q is 1,2-dihydro-2-oxoquinolin-3-yl, 1,2-dihydro-2-oxoquinolin-5-yl, 1,2-dihydro-2-oxoquinolin-6-yl or 1,2-dihydro-2-oxoquinolin-7-yl which may optionally bear one or two substituents selected from fluoro, chloro, methyl, ethyl, propyl, trifluoromethyl, 2-fluoroethyl, 2-dimethylaminoethyl and benzyl; and A, X, Ar, $R^1$, $R^2$ and $R^3$ have any of the meanings defined hereinbefore;

(g) Q is 1,2-dihydro-2-oxoquinolin-3-yl, 1,2-dihydro-2-oxoquinolin-5-yl, 1,2-dihydro-2-oxoquinolin-6-yl or 1,2-dihydro-2-oxoquinolin-7-yl which bears a 1-substituent selected from methyl, ethyl, propyl, 2-fluoroethyl, 2-dimethylaminoethyl and benzyl, and which may optionally bear a substituent selected from fluoro, chloro and trifluoromethyl; and A, X, Ar, $R^1$, $R^2$ and $R^3$ have any of the meanings defined hereinbefore;

(h) A is methylene, ethylene, trimethylene, 1-propenylene, 2-methylprop-1-enylene or 1-propynylene and Q, X, Ar, $R^1$, $R^2$ and $R^3$ have any of the meanings defined hereinbefore;

(i) A is methylene, 1-propenylene or 1-propynylene; and Q, X, Ar, $R^1$, $R^2$ and $R^3$ have any of the meanings defined hereinbefore;

(j) X is oxy and Q, A, Ar, $R^1$, $R^2$ and $R^3$ have any of the meanings defined hereinbefore;

(k) X is oxy or imino; and Q, A, Ar, $R^1$, $R^2$ and $R^3$ have any of the meanings defined hereinbefore;

(l) Ar is 1,3-phenylene or 1,4-phenylene which may optionally bear one substituent selected from fluoro, chloro, hydroxy, amino, nitro, methyl, methoxy, methylthio, methylsulphinyl, methylsulphonyl, methylamino, dimethylamino, trifluoromethyl, acetamido, cyanomethoxy and carbamoylmethoxy; and Q, A, X, $R^1$, $R^2$ and $R^3$ have any of the meanings defined hereinbefore;

(m) Ar is 1,3-phenylene or 1,4-phenylene which may optionally bear one or two susbitutents selected from fluoro, chloro, hydroxy, amino, nitro, ureido, methyl, methoxy, dimethylamino, trifluoromethyl, acetamido and cyanomethoxy; and Q, A, X, $R^1$, $R^2$ and $R^3$ have any of the meanings defined hereinbefore;

(n) Ar is 2,4-, 2,5-, 3,5- or 2,6-pyridylene or 4,6-pyrimidinylene which may optionally bear one substituent selected from chloro, methyl and methoxy; and Q, A, X, $R^1$, $R^2$ and $R^3$ have any of the meanings defined hereinbefore;

(o) Ar is 3,5-pyridylene or 3,5-pyridazinylene; and Q, A, X, $R^1$, $R^2$ and $R^3$ have any of the meanings defined hereinbefore;

(p) $R^1$ is hydrogen, methyl, ethyl, allyl, 2-propynyl or cyanomethyl; and Q, A, X, Ar, $R^2$ and $R^3$ have any of the meanings defined hereinbefore;

(q) $R^1$ is methyl, ethyl, allyl or 2-propynyl; and Q, A, X, Ar, $R^2$ and $R^3$ have any of the meanings defined hereinbefore;

(r) $R^2$ and $R^3$ together form a group of the formula —$A^2$—$X^2$—$A^3$— which, together with the carbon atom to which $A^2$ and $A^3$ are attached, defines a ring having 4 to 7 ring atoms, wherein $A^2$ and $A^3$, which may be the same or different, each is methylene, ethylene, trimethylene or tetramethylene and $X^2$ is oxy, thio, sulphinyl or sulphonyl, and which ring may bear a substituent selected from hydroxy, methyl, methoxy, ethoxy, methylthio, methylsulphinyl, methysulphonyl and methylenedioxy; and Q, A, X, Ar and $R^1$ have any of the meanings defined hereinbefore; or (s) $R^2$ and $R^3$ together form a group of the formula —$A^2$—$X^2$—$A^3$— which, together with the carbon atom to which $A^2$ and $A^3$ are attached defines a ring having 5 to 7 ring atoms, wherein $A^2$ and $A^3$, which may be the same or different, each is methylene, ethylene or trimethylene and $X^2$ is oxy, and which ring may bear one or two substituents selected from hydroxy, methyl, ethyl and methoxy; and Q, A, X, Ar and $R^1$ have any of the meanings defined hereinbefore;

or a pharmaceutically-acceptable salt thereof.

A particular compound of the invention comprises a heterocycle of the formula I wherein Q is pyridyl, pyrimidinyl, pyrazinyl, quinolyl, isoquinolyl, quinazolinyl or quinoxalinyl which may optionally bear one, two or three substitutents selected from fluoro, chloro, hydroxy, oxo, methyl, ethyl, propyl, trifluoromethyl, 2-fluoroethyl, 2-dimethylaminoethyl and benzyl;

wherein A is methylene, 1-propenylene or 1-propynylene;

wherein X is oxy or imino;

wherein Ar is 1,3-phenylene or 1,4-phenylene which may optionally bear one or two substituents selected from fluoro, chloro, hydroxy, amino, nitro, ureido, methyl, methoxy, dimethylamino, trifluoromethyl, acetamido and cyanomethoxy, or Ar is 3,5-pyridylene or 3,5-pyridazinylene;

wherein $R^1$ is methyl, ethyl, allyl or 2-propynyl; and wherein $R^2$ and $R^3$ together form a group of the formula —$A^2$—$X^2$—$A^3$— which, together with the carbon atom to which $A^2$ and $A^3$ are attached defines a ring having 5 to 7 ring atoms, wherein $A^2$ and $A^3$ which may be the same or different, each is methylene, ethylene or trimethylene and $X^2$ is oxy, and which ring may bear one or two substituents selected from hydroxy, methyl, ethyl and methoxy;

or a pharmaceutically-acceptable salt thereof.

A further particular compound of the invention comprises a heterocycle of the formula I wherein Q is 2-pyridyl, 3-pyridyl, 3-pyridazinyl, 2-pyrimidinyl or 2-pyrazinyl which may optionally bear one substituent selected from chloro, hydroxy, cyano, methyl, methoxy and trifluoromethyl, or Q is 2-quinolyl, 3-quinolyl, 6-quinolyl, 7-quinolyl, 3-isoquinolyl, 6-isoquinolyl, 7-isoquinolyl, 3-cinnolyl, 2-quinazolinyl, 6-quinazolinyl, 2-quinoxalinyl, 6-quinoxalinyl, 6-phthalazinyl, 1,7-naphthyridin-3-yl, 1-7-naphthyridin-6-yl, 1,8-naphthyridin-3-yl or 2,7-naphthyridin-3-yl which may optionally bear one or two substituents selected from fluoro, chloro, hydroxy, oxo, cyano, methyl, methoxy and trifluoromethyl;

A is methylene, ethylene, trimethylene, 1-propenylene, 2-methylprop-1-enylene or 1-propynylene;

X is oxy;

Ar is 1,3-phenylene or 1,4-phenylene which may optionally bear one substituent selected from fluoro, chloro, hydroxy, amino, nitro, methyl, methoxy, methylthio, methylsulphinyl, methylsulphonyl, methylamino, dimethylamino, trifluoromethyl, acetamido, cyanomethoxy and carbamoylmethoxy, or Ar is 2,4-, 2,5-, 3,5- or 2,6-pyridylene or 4,6-pyrimidinylene which may optionally bear one substituent selected from chloro, methyl and methoxy;

$R^1$ is methyl, ethyl, allyl or 2-propynyl; and

R² and R³ together form a group of the formula —A²—X²—A³— which, together with the carbon atom to which A² and A³ are attached, defines a ring having 4 to 7 ring atoms, wherein A² and A³, which may be the same or different, each is methylene, ethylene, trimethylene or tetramethylene and X² is oxy, thio, sulphinyl or sulphonyl, and which ring may bear a substituent selected from hydroxy, methyl, methoxy, ethoxy, methylthio, methylsulphinyl, methylsulphonyl and methylenedioxy;

or a pharmaceutically-acceptable salt thereof.

A further particular compound of the invention comprises a heterocycle of the formula I wherein Q is 3-quinolyl, 5-quinolyl, 6-quinolyl, 7-quinolyl, 3-isoquinolyl, 2-quinazolinyl, 6-quinazolinyl or 6-quinoxalinyl which may optionally bear one, two or three substituents selected from fluoro, hydroxy, oxo, methyl, ethyl, 2-fluoroethyl, 2-dimethylaminoethyl and benzyl;

wherein A is methylene;

wherein X is oxy or imino;

wherein Ar is 1,3-phenylene or 1,4-phenylene which may optionally bear one or two substituents selected from fluoro, hydroxy, amino, ureido, methoxy, trifluoromethyl and cyanomethoxy, or Ar is 3,5-pyridylene;

wherein R¹ is methyl, ethyl or allyl; and wherein R² and R³ together form a group of the formula —A²—X²—A³— which, together with the carbon atom to which A² and A³ are attached defines a ring having 5 or 6 ring atoms, wherein A² is ethylene, A³ is methylene or ethylene and X² is oxy, and which ring may bear one or two substituents selected from hydroxy, methyl and methoxy;

or a pharmaceutically-acceptable salt thereof.

A preferred compound of the invention comprises a heterocycle of the formula I wherein Q is 6-quinolyl, 3-isoquinolyl, 2-quinazolinyl, 6-quinazolinyl, 6-quinoxalinyl, 1,2-dihydro-2-oxoquinolin-3-yl, 1,2-dihydro-2-oxoquinolin-5-yl, 1,2-dihydro-2-oxoquinolin-6-yl or 1,2-dihydro-2-oxoquinolin-7-yl which may optionally bear one or two substituents selected from fluoro, methyl, ethyl, 2-fluoroethyl, 2-dimethylaminoethyl and benzyl;

wherein A is methylene;

wherein X is oxy;

wherein Ar is 1,3-phenylene or 1,4-phenylene which may optionally bear one or two substituents selected from fluoro, amino, ureido, methoxy and trifluoromethyl;

wherein R¹ is methyl, ethyl or allyl; and wherein R² and R³ together from a group of the formula —A²—X²—A³— which, together with the carbon atom to which A² and A³ are attached defines a ring having 5 or 6 ring atoms, wherein A² is ethylene, A³ is methylene or ethylene and X² is oxy, and which ring may bear one or two substituents selected from hydroxy, methyl and methoxy;

or a pharmaceutically-acceptable salt thereof.

A further preferred compound of the invention comprises a heterocycle of the formula I wherein Q is 1,2-dihydro-2-oxoquinolin-3-yl or 1,2-dihydro-2-oxoquinolin-6-yl which bears a 1-substituent selected from methyl, ethyl, 2-fluoroethyl and benzyl;

wherein A is methylene;

wherein X is oxy;

wherein Ar is 1,3-phenylene which may optionally bear one or two substituents selected from fluoro, amino and trifluoromethyl; wherein R¹ is methyl, ethyl or allyl; and wherein R² and R³ together form a group of the formula —A²—X²—A³— which, together with the carbon atom to which A² and A³ are attached defines a ring having 5 or 6 ring atoms, wherein A² is ethylene, A³ is methylene or ethylene and X² is oxy, and which ring may bear a methyl substituent alpha to X²;

or a pharmaceutically-acceptable salt thereof.

Specific especially preferred compounds of the invention include, for example, the following heterocycles of the formula I, or pharmaceutically-acceptable salts thereof:

4-methoxy-4-[3-(3-(2-pyridyl)prop-2-yn-1-yloxy)-phenyl]tetrahydropyran,

4-[5-fluoro-3-(3-(2-pyridyl)prop-2-yn-1-yloxy)phenyl]-4-methoxytetrahydropyran,

4-[5-fluoro-3-(quinoxalin-6-ylmethoxy)phenyl]-4-methoxytetrahydropyran, (2RS,4SR)-4-[5-fluoro-3-(quinoxalin-6-ylmethoxy)-phenyl]-4-methoxy-2-methyltetrahydropyran, 4-[3-(1,2-dihydro-1-methyl-2-oxoquinolin-3-ylmethoxy)phenyl]-4-methoxytetrahydropyran, 4-[5-fluoro-3-(6-quinolylmethoxy)phenyl]-4-methoxytetrahydropyran, 4-[3-(1,2-dihydro-1-methyl-2-oxoquinolin-6-ylmethoxy)phenyl]-4-methoxytetrahydropyran, 4-[5-fluoro-3-(1,2-dihydro-1-methyl-2-oxoquinolin-6-ylmethoxy)phenyl]-4-methoxytetrahydropyran, 4-allyloxy-4-[5-fluoro-3-(1,2-dihydro-1-methyl-2-oxoquinolin-6-ylmethoxy)phenyl]tetrahydropyran, 4-[5-fluoro-3-(1,2-dihydro-1-(2-fluoroethyl)-2-oxoquinolin-6-ylmethoxy)phenyl]-4-methoxytetrahydropyran, 4-[2,5-difluoro-3-(1,2-dihydro-1-methyl-2-oxoquinolin-6-ylmethoxy)phenyl]-4-methoxytetrahydropyran, 4-[3-(1,2-dihydro-1-methyl-2-oxoquinolin-6-ylmethoxy)-5-trifluoromethylphenyl]-4-methoxytetrahydropyran, 4-allyloxy-4-[3-(1,2-dihydro-1-methyl-2-oxoquinolin-6-ylmethoxy)-5-trifluoromethylphenyl]tetrahydropyran, (2RS,4SR)-4-[5-fluoro-3-(1,2-dihydro-1-methyl-2-oxoquinolin-6-ylmethoxy)phenyl]-4-methoxy-2-methyltetrahydropyran, (2RS,4SR)-4-[5-fluoro-3-(1,2-dihydro-1-ethyl-2-oxoquinolin-6-ylmethoxy)phenyl]-4-methoxy-2-methyltetrahydropyran, (2RS,4SR)-4-[5-amino-3-(1,2-dihydro-1-methyl-2-oxoquinolin-6-ylmethoxy)phenyl]-4-methoxy-2-methyltetrahydropyran, (2S,4R)-4-[3-(1,2-dihydro-1-methyl-2-oxoquinolin-6-ylmethoxy)phenyl]-4-methoxy-2-methyltetrahydropyran, (2S,4R)-4-[5-fluoro-3-(1,2-dihydro-1-methyl-2-oxoquinolin-6-ylmethoxy)phenyl]-4-methoxy-2-methyltetrahydropyran and (2RS,3SR)-3-[5-fluoro-3-(1,2-dihydro-1-ethyl-2-oxoquinolin-6-ylmethoxy)phenyl]-3-methoxy-2-methyltetrahydrofuran.

A compound of the invention comprising a heterocycle of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, Q, A, X, Ar, $R^1$, $R^2$ and $R^3$ have any of the meanings defined hereinbefore.

(a) The alkylation, in the presence of a suitable reagent, of a compound of the formula II with a compound of the formula Q—A—Z wherein Z is a displaceable group; provided that, when there is an amino, imino, alkylamino, hydroxy or carboxy group in Q, Ar, $R^1$, $R^2$ or $R^3$, any amino, imino, alkylamino or carboxy group is protected by a a conventional protecting group and any hydroxy group may be protected by a conventional protecting group or alternatively any hydroxy group need not be protected; whereafter any undesired protecting group in Q, Ar, $R^1$, $R^2$ or $R^3$ is removed by conventional means.

A suitable displaceable group Z is, for example, a halogeno, sulphonyloxy or hydroxy group, for example a chloro, bromo, iodo, methanesulphonyloxy or toluene-p-sulphonyloxy group.

A suitable reagent for the alkylation reaction when Z is a halogeno or sulphonyloxy group is, for example, a suitable base, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, $-10°$ to $150°$ C., conveniently at or near ambient temperature.

A suitable reagent for the alkylation reaction when Z is a hydroxy group is, for example, the reagent obtained when a compound of the formula Q—A—OH is reacted with a di-(1-4C)alkyl azodicarboxylate in the presence of a triarylphosphine, for example with diethyl azodicarboxylate in the presence of triphenylphosphine. The alkylation reaction is preferably performed in a suitable inert solvent or diluent, for example acetone, 1,2-dimethoxyethane or tetrahydrofuran, and at a temperature in the range, for example, $10°$ to $80°$ C., conveniently at or near ambient temperature.

A suitable protecting group for an amino, imino or alkylamino group is, for example, an acyl group for example a (1-4C)alkanoyl group (especially acetyl), a (1-4C)alkoxycarbonyl group (especially methoxycarbonyl, ethoxycarbonyl or t-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

Alternatively a suitable protecting group for an amino group is, for example, a benzylidene group formed by the reaction of the amino group and a benzaldehyde such as, for example, benzaldehyde itself. A benzylidene protecting group may be removed by, for example, oxidative hydrolysis in the presence of a suitable acid such as hydrochloric, sulphuric or phosphoric acid. A suitable oxidising agent is, for example, an alkali metal or alkaline earth metal cyanate such as, for example, sodium or potassium cyanate.

A suitable protecting group for a carboxy group is, for example, an esterifying group, for example a (1-4C)alkyl group (especially methyl or ethyl) or an arylmethyl group (especially benzyl). The deprotection conditions for the above protecting groups necessarily vary with the choice of protecting group. Thus, for example, an esterifying group such as an alkyl or arylmethyl group may be removed, for example, by hydrolysis with a suitable base such as an alkali metal hydroxide, for example lithium or sodium hydroxide. Alternatively an esterifying group such as an arylmethyl group may be removed, for example, by hydrogenation over a catalyst such as palladium-on-charcoal.

A suitable protecting group for a hydroxy group is, for example, an acyl group, for example a (1-4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula II may be obtained by standard procedures of organic chemistry. The preparation of examples of such starting materials is described within the accompanying non-limiting Examples which are provided for the purpose of illustration only. Other necessary starting materials are obtainable by analogous procedures to those described or by modification thereto which are within the ordinary skill of an organic chemist. Thus the starting material of the formula II may be obtained, for example, by deprotecting a protected heterocycle of the formula III wherein $R^4$ is a protecting group and X, Ar, $R^1$, $R^2$ and $R^3$ have the meanings defined hereinbefore.

A suitable protecting group $R^4$ is, for example, an arylmethyl group (especially benzyl), a tri-(1-4C)alkylsilyl group (especially trimethylsilyl or t-butyldimethylsilyl), an aryldi-(1-4C)alkylsilyl group (especially dimethylphenylsilyl), a (1-4C)alkyl group (especially methyl), a (1-4C)alkoxymethyl group (especially methoxymethyl) or a tetrahydropyranyl group (especially tetrahydropyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryldialkylsilyl group such as a t-butyldimethylsilyl or a dimethylphenylsilyl group may be removed, for example, by treatment with a suitable acid such as hydrochloric, sulphuric, phosphoric or trifluoroacetic acid or with an alkali metal or ammonium fluoride such as sodium fluoride or, preferably, tetrabutylammonium fluoride. Alternatively an alkyl group may be removed, for example, by treatment with an alkali metal (1-4C)alkylsulphide such as sodium thioethoxide or, for example, by treatment with an alkali metal diarylphosphide such as lithium diphenylphosphide or, for example, by treatment with a boron or aluminium trihalide such as boron tribromide. Alternatively a (1–4C)alkoxymethyl group or tetrahydropyranyl group may be removed, for example, by treatment with a suitable acid such as hydrochloric or trifluoroacetic acid.

The protecting group $R^4$ may be, for example, a tri-(1–4C)alkylsilyl group which can be removed while the protecting group for any amino, imino, alkylamino, carboxy or hydroxy group in Ar, $R^1$, $R^2$ or $R^3$ is retained.

The protected starting material of the formula III may be obtained by standard procedures of organic chemistry as illustrated in the accompanying non-limiting Examples. Thus, for example the protected starting material of the formula III, wherein $R^4$ has the meaning defined hereinbefore, may be obtained by the alkylation of the tertiary alcohol of the formula IV with an alkylating agent of the formula $R^1$—Z, wherein Z is a displaceable group as defined hereinbefore other than hydroxy, in the presence of a suitable base as defined hereinbefore, and provided that any amino, imino, alkylamino or hydroxy group in Ar, $R^2$ or $R^3$ is protected by a conventional protecting group.

The tertiary alcohol starting material of the formula IV may be obtained by the reaction of a compound of the formula $R^4$—X—Ar—Z, wherein $R^4$ and Ar have the meanings defined hereinbefore and Z is a halogeno group as defined hereinbefore and provided that any amino, alkylamino or hydroxy group in Ar is protected with a conventional protecting group, with either an organometallic compound of the formula $R^5$—M, wherein $R^5$ is a (1–6C)alkyl group such as butyl and M is a metallic group, for example lithium, to give an organometallic compound of the formula $R^4$—X—Ar—M, or with a metal such as magnesium to give an organometallic compound of the formula $R^4$—X—Ar—M—Z; whereafter either of these organometallic compounds may be reacted with a ketone of the formula $R^2$—CO—$R^3$, wherein $R^2$ and $R^3$ have the meanings defined hereinbefore, and provided that any imino or hydroxy group in $R^2$ and $R^3$ is protected by a conventional protecting group.

(b) The alkylation, in the presence of a suitable base as defined hereinbefore, of a compound of the formula V with a compound of the formula $R^1$—Z, wherein $R^1$ and Z have the meanings defined hereinbefore, provided that, when there is an amino, imino, alkylamino, hydroxy or carboxy group in Q, X, Ar, $R^2$ or $R^3$, any amino, imino, alkylamino, hydroxy or carboxy group is protected by a conventional protecting group; whereafter any undesired protecting group in Q, X, Ar, $R^2$ or $R^3$ is removed by conventional means.

The starting materials of the formula V may be obtained by standard procedures of organic chemistry. The preparation of examples of such starting materials is described within the accompanying non-limiting Examples which are provided for the purpose of illustration only. Other necessary starting materials are obtainable by analogous procedures to those described or by modification thereto which are within the ordinary skill of an organic chemist. Thus the tertiary alcohol starting material of the formula V may be obtained, for example, by the alkylation, in the presence of a suitable base, of a compound of the formula HX—Ar—Z, wherein Ar has the meaning defined hereinbefore and Z is a halogeno group as defined hereinbefore, with a compound of the formula Q—A—Z, wherein Q, A and Z have the meanings defined hereinbefore, and provided that any amino, alkylamino, carboxy or hydroxy group in Q or Ar is protected by a conventional protecting group, to give a compound of the formula Q—A—X—Ar—Z. Alternatively the compound of the formula Q—A—X—Ar—Z may be obtained, for example, by the alkylation, in the presence of a suitable base, of a compound of the formula Q—A—XH, wherein Q, A and X have the meanings defined hereinbefore, with a compound of the formula Z—Ar—Z, wherein Z and Ar have the meanings defined hereinbefore. The product so obtained may be treated either with an organometallic compound of the formula $R^5$—M, wherein $R^5$ is a (1–6C)alkyl group such as butyl and M is a metallic group, for example lithium, to give an organometallic compound of the formula Q—A—X—Ar—M, or with a metal such as magnesium to give an organometallic compound of the formula Q—A—X—Ar—M—Z. Either of these organometallic compounds may be reacted with a ketone of the formula $R^2$—CO—$R^3$, provided that any imino or hydroxy group in X, $R^2$ or $R^3$ is protected by a conventional protecting group, to give the required tertiary alcohol starting material of the formula V.

(c) For the production of those compounds of the formula I wherein A is a (3–6C)alkynylene group, the coupling, in the presence of a suitable organometallic catalyst, of a heterocyclic compound of the formula Q—Z, wherein Q has the meaning defined hereinbefore and Z is a halogeno group such as iodo, with an ethynyl compound of the formula VI, wherein $A^1$ is (1–4C)alkylene and X, Ar, $R^1$, $R^2$ and $R^3$ have the meanings defined hereinbefore.

A suitable organometallic catalyst is, for example, any agent known in the art for such a coupling reaction. Thus, for example, a suitable reagent is formed when, for example, bis(triphenylphosphine)palladium chloride or tetrakis(triphenylphosphine)palladium, and a copper halide, for example cuprous iodide, are mixed. The coupling is generally carried out in a suitable inert solvent or diluent, for example acetonitrile, 1,2-dimethoxyethane, toluene or tetrahydrofuran, at a temperature in the range, for example, 10° to 80° C., conveniently at or near 30° C., and in the presence of a suitable base such as, for example, a tri-(1–4C)alkylamine such as triethylamine, or a cyclic amine such as piperidine.

The ethynyl compound of the formula VI, used as a starting material, may be obtained, for example, by the alkylation, in the presence of a suitable base, of a compound of the formula II, wherein X, Ar, $R^1$, $R^2$ and $R^3$ have the meanings defined hereinbefore, with an alkylating agent of the formula H—C≡C—$A^1$—Z, wherein $A^1$ has the meaning defined hereinbefore and Z is a halogeno group, and provided that any amino, alkylamino, carboxy or hydroxy group in Ar, $R^1$, $R^2$ or $R^3$ is protected by a conventional protecting group.

(d) For the production of those compounds of the formula I wherein Ar bears an alkylsulphinyl or alkylsulphonyl substituent, wherein X is a sulphinyl or sulphonyl group, or wherein $R^2$ and $R^3$ together form a group of the formula —$A^2$—$X^2$—$A^3$— which bears one or two alkylsulphinyl or alkylsulphonyl groups and $X^2$ is a sulphinyl or sulphonyl group, the oxidation of a compound of the formula I wherein Ar bears an alkylthio substituent, or wherein $R^2$ and $R^3$ together form a group of the formula —$A^2$—$X^2$—$A^3$— which bears one or two alkylthio groups and wherein $X^2$ is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or t-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(e) For the production of those compounds of the formula I wherein Ar bears an alkanoylamino substituent, the acylation of a compound of the formula I wherein Ar bears an amino substituent.

A suitable acylating agent is, for example, any agent known in the art for the acylation of amino to acylamino, for example an acyl halide, for example a (2-6C)alkanoyl chloride or bromide, in the presence of a suitable base, an alkanoic acid anhydride, for example a (2-6C)alkanoic acid anhydride, or an alkanoic acid mixed anhydride, for example the mixed anhydride formed by the reaction of an alkanoic acid and a (1-4C)alkoxycarbonyl halide, for example a (1-4C)alkoxycarbonyl chloride, in the presence of a suitable base. In general the reaction is carried out in a suitable solvent or diluent such as methylene chloride, acetone, tetrahydrofuran or t-butyl methyl ether and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

(f) For the production of those compounds of the formula I wherein $R^1$ is alkanoyl or benzoyl optionally bearing a substituent as defined hereinbefore, the acylation of a compound of the formula I wherein $R^1$ is hydrogen. For the production of those compounds of the formula I wherein $R^1$ is alkanoyl the acylation reaction may be carried out using, for example, a suitable acylating agent as defined hereinbefore. For the production of those compounds of the formula I wherein $R^1$ is benzoyl optionally bearing a substituent the acylation may be carried out using, for example, a benzoyl halide, for example a benzoyl chloride or bromide, in the presence of a suitable base as defined hereinbefore.

(g) For the production of those compounds of the formula I wherein A is alkenylene or $R^1$ is alkenyl, the reduction of the corresponding compound wherein A is alkynylene or $R^1$ is alkynyl. In general conditions which are standard in the art for the reduction of an alkynyl or alkynylene group are used. Thus, for example, the reduction may be carried out by the hydrogenation of a solution of the alkynyl or alkynylene compound in an inert solvent or diluent in the presence of a suitable metal catalyst. A suitable inert solvent is, for example, an alcohol, for example methanol or ethanol, or an ether, for example tetrahydrofuran or t-butyl methyl ether. A suitable metal catalyst is, for example, palladium or platinum on an inert support, for example charcoal or barium sulphate.

Preferably a palladium-on-barium sulphate catalyst is used to substantially prevent over-reduction of the alkynyl or alkynylene group to an alkyl or alkylene group respectively. The reaction is generally carried out at a temperature at or near ambient temperature, that is in the range 15° to 35° C.

Alternatively the reduction may be carried out by treating a solution of the alkynyl or alkynylene compound in an inert solvent or diluent with a suitable mixture such as a 1:1 mixture of an organometallic hydride, for example a di-(1-6C)alkylaluminium hydride such as diisobutylaluminium hydride, and an alkyl metal, for example a (1-6C)alkyl lithium such as methyl lithium. A suitable inert solvent or diluent is, for example, tetrahydrofuran, diethyl ether or t-butyl methyl ether and, in general, the reaction is carried out at a temperature, for example, in the range $-25°$ C. to ambient temperature (especially $-10°$ to $10°$ C.).

(h) For the production of those compounds of the formula I wherein Q bears an alkyl or substituted alkyl substituent on an available nitrogen atom, or wherein Ar bears an alkoxy or substituted alkoxy substituent, the alkylation of a compound of the formula I wherein Q bears a hydrogen atom on said available nitrogen atom, or wherein Ar bears a hydroxy substituent.

A suitable alkylating agent is, for example, any agent known in the art for the alkylation of an available nitrogen atom, or of hydroxy to alkoxy or substituted alkoxy, for example an alkyl or substituted alkyl halide, for example a (1-6C)alkyl chloride, bromide or iodide or a substituted (1-4C)alkyl chloride, bromide or iodide, in the presence of a suitable base. A suitable base for the alkylation reaction is, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 10° to 150° C., conveniently at or near ambient temperature.

(i) For the production of those compounds of the formula I wherein Q or Ar bears an amino substituent, the reduction of a compound of the formula I wherein Q or Ar bears a nitro substituent.

A suitable reducing agent is, for example, any agent known in the art for the reduction of a nitro group to an amino group. Thus, for example, the reduction may be carried out by the hydrogenation of a solution of the nitro compound in an inert solvent or diluent in the presence of a suitable metal catalyst, for example finely divided platinum metal (obtained by the reduction of platinum oxide in situ). A suitable inert solvent or diluent is, for example, an alcohol, for example methanol, ethanol or isopropanol, or an ether, for example tetrahydrofuran.

A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal in a suitable solvent or diluent such as a mixture of water and an alcohol, for example, methanol or ethanol, to a temperature in the range, for example 50° to 150° C., conveniently at or near 70° C.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, as illustrated in the accompanying non-limiting Examples, or by resolution of a racemic form of said compound using a conventional procedure.

Many of the intermediates defined herein are novel, for example those of the formula V and these are provided as a further feature of the invention.

As stated previously, the heterocycles of the formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512-11519). This test provides a measure of the intrinsic inhibitory properties against soluble 5-LO in an extracellular environment.

b) An in vitro assay system involving incubating a test compound with heparinised human blood, prior to challenge with the calcium inonphore A23187 and then indirectly measuring the inhibitory effects on 5-LO by assaying the amount of LTB$_4$ using the specific radioimmunoassay described by Carey and Forder (F. Carey and R. A. Forder, *Brit. J. Pharmacol.* 1985, 84, 34P) which involves the use of a protein-LTB$_4$ conjugate produced using the procedure of Young et alia (*Prostaglandins*, 1983, 26(4), 605-613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane B$_2$(TxB$_2$) described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of LTB$_4$ and TxB$_2$. This test provides an indication of the bioavailability of a test compound as an inhibitor of 5-LO or cyclooxygenase.

d) An in vitro assay system involving the measurement of the inhibitory properties of a test compound against the liberation of LTC$_4$ and PGE$_2$ induced by zymosan on mouse resident peritoneal macrophages, using the procedure of Humes (J. L. Humes et alia, *Biochem. Pharmacol.*, 1983, 32, 2319-2322) and conventional radioimmunoassay systems to measure LTC$_4$ and PGE$_2$. This test provides an indication of inhibitory effects against 5-LO and cyclooxygenase in a non-proteinaceous system.

e) An in vivo system involving the measurement of the effects of a test compound in inhibiting the inflammatory response to arachidonic acid in the rabbit skin model developed by D. Aked et alia (*Brit. J. Pharmacol.*, 1986, 89, 431-438). This test provides an in vivo model for 5-LO inhibitors administered topically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a betaadrenergic blocking agent (propranolol) and a cyclooxygenase inhibitor (indomethacin), using the procedure of W. H. Anderson et alia (*British J. Pharmacology*, 1983, 78(1), 67-574). This test provides a further in vivo test for detecting 5-LO inhibitors.

Although the pharmacological properties of the compounds of the formula I vary with structural changes as expected, in general compounds of the formula I possess 5-LO inhibitory effects at the following concentrations or doses in one or more of the above tests a)-f):

Test a):
IC$_{50}$ in the range, for example, 0.01-30 micromolar;

Test b): IC$_{50}$ (LTB$_4$) in the range, for example, 0.01-40 micromolar,
IC$_{50}$ (TxB$_2$) in the range, for example, 40-200 micromolar;

Test c): oral ED$_{50}$(LTB$_4$) in the range, for example, 5-200 mg/kg;

Test d):
IC$_{50}$ (LTC$_4$) in the range, for example, 0.001-1 micromolar,
IC$_{50}$ (PGE$_2$) in the range, for example, 20-1000 micromolar;

Test e): inhibition of inflammation in the range, for example, 0.3-100 micrograms intradermally;

Test f): ED$_{50}$ in the range, for example, 0.5-10 mg/kg i.v.

No overt toxicity or other untoward effects are present in tests c), e) and/or f) when compounds of the formula I are administered at several multiples of their minimum inhibitory dose or concentration.

Thus, by way of example, the compound 4-methoxy-4-[3-(3-(2-pyridyl)prop-2-yn-1-yloxy)phenyl]tetrahydropyran has an IC$_{50}$ of 2.0 micromolar against LTB$_4$ and of >40 micromolar against TxB$_2$ in test b), and an oral ED$_{50}$ of <100 mg/kg against LTB$_4$ in test c), the compound 4-[5-fluoro-3-(6-quinolylmethoxy)phenyl]-4-methoxytetrahydropyran has an IC$_{50}$ of 0.1 micromolar against LTB$_4$ in test b), and an oral ED$_{50}$ of 8 mg/kg against LTB$_4$ in test c), and the compound 4-[3-(1,2-dihydro-1-methyl-2-oxoquinolin-6-ylmethoxy)phenyl]-4-methoxytetrahydropyran has an IC$_{50}$ of 0.03 micromolar against LTB$_4$ in test b), and an oral ED$_{50}$ of 3 mg/kg against LTB$_4$ in test c). In general those compounds of the formula I which are particularly preferred have an IC$_{50}$ of <1 micromolar against LTB$_4$ and of >40 micromolar against TxB$_2$ in test b), and an oral ED$_{50}$ of <100 mg/kg against LTB$_4$ in test c).

These compounds are examples of heterocycles of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a heterocycle of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a heterocycle of the formula I or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a heterocycle of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a heterocycle of the formula I will naturally vary according to the nature and severity of the conditions, the age and sex of the animal or patient and the route of administration, according to well known principles of medicine. As mentioned above, heterocycles of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a heterocycle of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The compounds of the formula I may also be used in combination with leukotriene antagonists such as those disclosed in European Patent Specification Nos. 179619, 199543, 220066, 227241, 242167, 290145, 337765, 337766 and 337767, which are incorporated herein by way of reference.

The invention will now be illustrated in the following non-limiting Examples in which, unless otherwise stated:

(i) evaporations were carried out by rotary evaporations in vacuo and work-up procedures were carried out after removal of residual solids by filtration;

(ii) operations were carried out at room temperature, that is in the range 18°–20° and under an atmosphere of an inert gas such as argon;

(iii) column chromatography (by the flash procedure) and medium pressure liquid chromatography (MPLC) were performed on Merck Kieselgel silica (Art. 9385) obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture; and (viii) the specific rotation, $[alpha]^t$, of plane polarised light was determined using the sodium D line (5890 Angstroms), at 20° C., and generally using sample concentrations of approximately 1 g/100 ml of solvent.

EXAMPLE 1

A mixture of 3-bromomethyl-1,2-dihydro-1-methylquinolin-2-one (3 g), 4-(3-hydroxyphenyl)-4-methoxytetrahydropyran (2.1 g), potassium carbonate (1.67 g) and dimethylformamide (16 ml) was stirred at ambient temperature for 15 hours. The mixture was partitioned between methylene chloride and water. The organic layer was washed with a saturated aqueous sodium chloride solution, dried (MgSO$_4$) and evaporated. The residue was purified by column chromatography using a 1:1 v/v mixture of toluene and ethyl acetate as eluent. There was thus obtained 4-[3-(1,2-dihydro-1-methyl-2-oxoquinolin-3-ylmethoxy)phenyl]-4-methoxytetrahydropyran (3.5 g, 92%), m.p. 135° C.

The 3-bromomethyl-1,2-dihydro-1-methylquinolin-2-one starting material was obtained as follows:

Sodium hydride (55% w/w suspension in oil; 0.268 g) was added portionwise to a stirred suspension of 1,2-dihydro-2-oxoquinoline-3-carbaldehyde (1 g) in dimethylformamide (10 ml) which had been cooled in an ice bath. The mixture was allowed to warm to ambient temperature and was then heated to 60° C. for 1 hour. The mixture was recooled in an ice bath and methyl iodide (0.41 ml) was added. Dimethylformamide (50 ml) was added and the mixture was stirred at ambient temperature for 16 hours. The mixture was poured into water (50 ml) and extracted with methylene chloride (3×50 ml). The combined extracts were washed with water (50 ml) and evaporated. The residue was triturated under diethyl ether to give 1,2-dihydro-1-methyl-2-oxoquinoline-3-carbaldehyde as a pale yellow solid (0.81 g, 74%).

The product so obtained was converted to 3-bromomethyl-1,2-dihydro-1-methylquinolin-2-one using the known procedure (*Chem. Pharm. Bull.*, 1985, 33, 3775) for the conversion of 1,2-dihydro-2-oxoquinoline-3-carbaldehyde to 3-bromomethyl-1,2-dihydroquinolin-2-one.

The 4-(3-hydroxyphenyl)-4-methoxytetrahydropyran used as a starting material was obtained as follows: 3-Methoxymethoxyphenyl bromide was prepared by the reaction of 3-bromophenol and dimethoxymethane using the general procedure described in *Synthesis*, 1976, 244. A Grignard reagent was prepared by heating a mixture of 3-methoxymethoxyphenyl bromide (6 g), magnesium (0.66 g) and tetrahydrofuran (34 ml) to 30° C. for 2 hours. The reagent was cooled to ambient temperature and a solution of tetrahydropyran-4-one (2.76 g) in tetrahydrofuran (2 ml) was added dropwise. The mixture was stirred at ambient temperature for 15 hours and evaporated. The residue was partitioned between ethyl acetate and water. The organic layer was washed with a saturated aqueous sodium chloride solution, dried (MgSO$_4$) and evaporated. The residue was purified by column chromatography using a 9:1 v/v mixture of methylene chloride and diethyl ether as eluent. There was thus obtained 4-hydroxy-4-(3-methoxymethoxyphenyl)tetrahydropyran (4.5 g, 69%), as an oil.

A mixture of the product so obtained, sodium hydride (55% w/w dispersion in mineral oil, 0.74 g) and tetrahydrofuran (50 ml) was stirred at ambient temperature for 15 minutes. Methyl iodide (1.42 ml) and 1,4,7,10,13-pentaoxacyclopentadecane (hereinafter 15-crown-5, 0.1 g) were added and the mixture was stirred at ambient temperature for 15 hours. The mixture was evaporated and the residue was partitioned between methylene chloride and water. The organic layer was separated, washed with water, dried (MgSO$_4$) and evaporated. There was thus obtained 4-methoxy-4-(3-methoxymethoxyphenyl)tetrahydropyran (1.23 g, 91%), as an oil.

A mixture of the product so obtained, concentrated hydrochloric acid (10 ml), isopropanol (40 ml) and tetrahydrofuran (160 ml) was stirred at ambient temperature for 15 hours. The mixture was evaporated and the residue was partitioned between ethyl acetate and water. The organic layer was washed with a saturated aqueous sodium chloride solution, dried (MgSO$_4$) and evaporated. The residue was purified by column chromatography using a 4:1 v/v mixture of methylene chloride and diethyl ether as eluent. There was thus obtained 4-(3-hydroxyphenyl)-4-methoxytetrahydropyran (0.57 g, 56%), as a colourless oil.

EXAMPLE 2

The alkylation reaction described in Example 1 was repeated except that the appropriate alkyl halide was used in place of 3-bromomethyl-1,2-dihydro-1-methylquinolin-2-one and the appropriate phenol was used in place of 4-(3-hydroxyphenyl)-4-methoxytetrahydropyran. There were thus obtained the compounds described in the following table:

TABLE I

Q—A—O—Ar—[cyclic structure with OMe and O]

| Ex. 2 Compd. No. | Q | A | Ar | Yield (%) | m.p. (°C.) |
|---|---|---|---|---|---|
| 1[a] | 2-pyridyl | —C≡C—CH$_2$— | 1,3-phenylene | 56 | oil* |
| 2[b,c] | 2-pyridyl | —CH$_2$— | 5-fluoro-1,3-phenylene | 46 | oil** |
| 3[c,d] | 6-quinoxalinyl | —CH$_2$— | 5-fluoro-1,3-phenylene | 55 | 83–85 |
| 4[c,e] | 1,2-dihydro-2-oxoquinolin-3-yl | —CH$_2$— | 5-fluoro-1,3-phenylene | 12 | oil+ |
| 5[f] | 1,2-dihydro-1-methyl-2-oxo-quinolin-3-yl | —CH$_2$— | 5-hydroxy-1,3-phenylene | 11 | 195–197 |
| 6[g] | 1,2-dihydro-1-methyl-2-oxo-quinolin-3-yl | —CH$_2$— | 5-cyanomethoxy-1,3-phenylene | 80 | 142 |
| 7[h] | 1,2-dihydro-1-methyl-2-oxo-quinolin-3-yl | —CH$_2$— | 3,5-pyridylene | 72 | 124 |

Notes a. 3-(2-Pyridyl)prop-2-yn-1-yl bromide hydrobromide used as a starting material was obtained as follows:

2-Propynyl alcohol (35 ml) was added dropwise to a stirred mixture of 2-bromopyridine (23.7 g), bis(triphenylphosphine)palladium chloride (1.54 g), triethylamine (21 ml), cuprous iodide (1.5 g) and acetonitrile (150 ml) and the mixture was stirred at ambient temperature for 30 minutes and then heated to 60° C. for 2 hours. The mixture was cooled to ambient temperature, poured into water (200 ml) and neutralised by adding dilute aqueous hydrochloric acid.

The mixture was extracted with methylene chloride (2×500 ml) and the combined extracts were washed with water (500 ml), dried (MgSO$_4$) and evaporated. The residue was purified by column chromatography eluting with a 1:1 v/v mixture of methylene chloride and ethyl acetate to give 3-(2-pyridyl)prop-2-yn-1-yl alcohol (14 g, 70%), m.p. 78°–80° C. (recrystallised from a mixture of hexane and ethyl acetate). A solution of bromine (3.1 ml) in methylene chloride (3 ml) was added to a mixture of triphenylphosphine (10.1 g) and methylene chloride (72 ml) which had been cooled to −8° C. in a salted ice-bath. A solution of the alcohol (4.8 g) obtained immediately above in methylene chloride (36 ml) was added and the mixture was stirred for 10 minutes and cooled to approximately −10° C. The mixture was filtered to give 3-(2-pyridyl)prop-2-yn-1-yl bromide hydrobromide (5.8 g, 58%), m.p. 112°–114° C., which was used without further purification.

b. 2-Chloromethylpyridine hydrochloride was used as the alkylating agent.

c. 4-(5-Fluoro-3-hydroxyphenyl)-4-methoxytetrahydropyran used as a starting material was obtained as follows:

Sodium hydride (50% w/w dispersion in mineral oil, 12.4 g) was added portionwise to a mixture of benzyl alcohol (26.7 ml) and dimethylacetamide (500 ml) and the mixture was stirred at ambient temperature for 1 hour. 1-Bromo-3,5-difluorobenzene (50 g) was added carefully to control the vigour of the ensuing exothermic reaction. The mixture was stirred at ambient temperature for 2 hours and the solvent was evaporated. The residue was partitioned between methylene chloride and water and the organic phase was washed with water (4×50 ml), dried (MgSO$_4$) and evaporated. The residue was purified by distillation to give 3-benzyloxy-1-bromo-5-fluorobenzene (41.8 g, 57%), as a colourless liquid (b.p. 124°–130° C. at 0.3 mm Hg).

A solution of a portion (9.75 g) of this product in tetrahydrofuran (150 ml) was cooled to −75° C. and n-butyl-lithium (1.6M in hexane, 22 ml) was added dropwise. The mixture was stirred at −75° C. for 1 hour and a solution of tetrahydropyran-4-one (3.47 g) in tetrahydrofuran (10 ml) was added dropwise. The mixture was stirred at −75° C. for 1 hour and then allowed to warm to 0° C. A saturated aqueous ammonium chloride solution (50 ml) was added and the organic phase was separated, dried (MgSO$_4$) and evaporated. The residue was purified by column chromatography using a 1:1 v/v mixture of toluene and ethyl acetate as eluent. There was thus obtained 4-(3-benzyloxy-5-fluorophenyl)-4-hydroxytetrahydropyran (7.4 g, 71%) as an oil.

After appropriate repetition of the above-mentioned reaction the product so obtained (12.1 g) was dissolved in tetrahydrofuran (150 ml) and sodium hydride (50% w/w dispersion in mineral oil, 2.11 g) was added portionwise. The mixture was stirred at ambient temperature for 1 hour, cooled in an ice-bath and methyl iodide (3.75 ml) was added dropwise. The mixture was stirred at ambient temperature for 18 hours, 2N aqueous hydrochloric acid (3 drops) were added and the organic solvent was evaporated. The residue was partitioned between ethyl acetate and water. The organic phase was separated, washed with water and with a saturated aqueous sodium chloride solution, dried (MgSO$_4$) and evaporated. There was thus obtained 4-(3-benzyloxy-5-fluorophenyl)-4-methoxytetrahydropyran (12.5 g, 99%), as a pale yellow oil which was used without further purification.

A solution of the product so obtained in ethanol (100 ml) was hydrogenated in the presence of 10% palladium-on-charcoal catalyst for 3 hours. The mixture was filtered and the filtrate was evaporated. There was thus obtained 4-(5-fluoro-3-hydroxyphenyl)-4-methoxytetrahydropyran (7.7 g, 86%), m.p. 123°–124° C.

d. 6-Bromomethylquinoxaline, used as the alkylating agent, is described in *J. Het. Chem.*, 1974, 11, 595.

e. 3-Bromomethyl-1,2-dihydroquinolin-2-one (*Chem. Pharm. Bull.*, 1985, 33, 3775) was used as the alkylating agent.

f. 4-(3,5-Dihydroxyphenyl)-4-methoxytetrahydropyran used as the phenolic starting material was obtained as follows:

3,5-Dihydroxyiodobenzene (*Tex. J. Sci.*, 1977, 28, 253) was reacted with two equivalents of benzyl bromide using the procedure described in Example 1 to give 3,5-dibenzyloxyiodobenzene as an oil in 96% yield. This was reacted with n-butyl-lithium using the procedure described in Note c. immediately above except that the reaction was carried out at −110° C. The organometallic reagent so formed was reacted with tetrahydropyran-4-one using the procedure described in that Note; the product was methylated and that product was hydrogenolysed using the procedure also described in Note c. immediately above. There was thus obtained 4-(3,5-dihydroxyphenyl)-4-methoxytetrahydropyran in 40% yield from 3,5-dibenzyloxyiodobenzene.

g. The appropriate phenol was obtained as follows:

4-(3,5-Dihydroxyphenyl)-4-methoxytetrahydropyran was reacted with one equivalent of iodoacetonitrile using the procedure described in Example 1 to give 4-(3-cyanomethoxy-5-hydroxyphenyl)-4-methoxytetrahydropyran (27%) as an oil.

h. The alkylation reaction was carried out at −20° C. for 15 hours and sodium hydride was used in place of potassium carbonate as the reaction base.

The appropriate phenol was obtained as follows:

3,5-Dibromopyridine was reacted with one equivalent of benzyl alcohol to give 3-benzyloxy-5-bromopyridine (56%) using the procedure described in the first paragraph of Note c. immediately above. That product was reacted with n-butyl-lithium using the procedure described in the second paragraph of Note c. except that the reaction was carried out at −110° C. The organometallic reagent so formed was reacted with tetrahydropyran-4-one using the procedure described in that Note; the product was methylated and that product was hydrogenolysed using the procedures also described in Note c. immediately above. There was thus obtained 4-(5-hydroxypyrid-3-yl)-4-methoxytetrahydropyran in 47% yield from 3-benzyloxy-5-bromopyridine.

\* NMR Spectrum: (CDCl$_3$, delta values) 1.57–2.07(m, 4H), 2.99(s, 3H), 3.77–3.83(m, 4H), 4.95(s, 2H), 7.03–7.63(m, 7H), 8.6(d, 1H).

\*\* NMR Spectrum: (CDCl$_3$, delta values) 1.9(m, 4H), 2.95(s, 3H), 3.85 (m, 4H), 5.2(s, 2H), 6.6–6.85(m, 3H), 7.25(t, 2H), 7.5(d, 1H), 7.75(t, 1H).

+NMR Spectrum: (CD$_3$SOCD$_3$, delta values) 1.8–2.0(m, 4H), 2.9(s, 3H), 3.6–3.8(m, 4H), 5.0(s, 2H), 6.75–6.9(m, 3H), 7.15–8.1(m, 5H).

EXAMPLE 3

Triethylamine (0.35 ml) was added to a mixture of 4-[5-fluoro-3-(2-propynyloxy)phenyl]-4-methoxytetrahydropyran (0.61 g), 2-iodopyridine (0.52 g), bis(triphenylphosphine)palladium chloride (0.03 g), cuprous iodide (0.03 g) and acetonitrile (12 ml) and the mixture was stirred at ambient temperature for 5 hours. The mixture was partitioned between ethyl acetate and water. The organic phase was separated and the aqueous phase was extracted with further ethyl acetate. The combined organic extracts were washed with water, dried (MgSO$_4$) and evaporated. The residue was purified by column chromatography using a 1:1 v/v mixture of toluene and ethyl acetate as eluent. There was thus obtained 4-[5-fluoro-3-(3-(2-pyridyl)prop-2-yn-1-yloxy)phenyl]-4-methoxytetrahydropyran (0.47 g, 60%), as a pale yellow oil.

NMR Spectrum (CDCl$_3$, delta values) 1.95 (m, 4H), 3.0 (s, 3H), 3.8 (m, 4H), 4.95 (s, 2H), 6.72 (t, 2H), 6.87 (s, 1H), 7.3 (broad s, 2H), 7.68 (broad s, 1H), 8.6 (broad s, 1H).

4-[5-Fluoro-3-(2-propynyloxy)phenyl]-4-methoxytetrahydropyran, used as a starting material, was obtained by the alkylation of 4-(5-fluoro-3-hydroxyphenyl)-4-methoxytetrahydropyran with 2-propynyl bromide using the procedure described for the alkylation reaction described in Example 1 except that acetone was used in place of dimethylformamide as the reaction solvent. The product was obtained in 95% yield, m.p. 75°–76° C.

EXAMPLE 4

The alkylation reaction described in Example 1 was repeated except that 6-bromomethylquinoxaline was used in place of 3-bromomethyl-1,2-dihydro-1-methylquinolin-2-one and (2RS,4SR)-4-(5-fluoro-3-hydroxyphenyl)-4-methoxy-2-methyltetrahydropyran was used in place of 4-(3-hydroxyphenyl)-4-methoxytetrahydropyran. There was thus obtained (2RS,4SR)-4-[5-fluoro-3-(quinoxalin-6-ylmethoxy)phenyl]-4-methoxy-2-methyltetrahydropyran, as an oil (45%).

NMR Spectrum: (CDCl$_3$, delta values) 1.21 (d, 3H), 1.54 (doublet of doublets, 1H), 1.80–2.03 (m, 3H), 2.98 (s, 3H), 3.77–3.97 (m, 3H), 5.30 (s, 2H), 6.66 (doublet of triplets, 1H), 6.74 (doublet of triplets, 1H), 6.87 (t, 1H), 7.85 (doublet of doublets, 1H), 8.18 (m, 2H), 8.89 (s, 2H);

Mass Spectrum: P m/e 382;

Elemental Analysis: Found C, 68.8; H, 6.2; N, 6.6; C$_{22}$H$_{23}$FN$_2$O$_3$ requires C, 69.1; H, 6.1; N, 7.3%.

The (2RS,4SR)-4-(5-fluoro-3-hydroxyphenyl)-4-methoxy-2-methyltetrahydropyran used as a starting material was obtained by way of the procedures described in the first two paragraphs of Note c. below Table I in Example 2, except that 2-methyltetrahydropyran-4-one (*J. Amer. Chem. Soc.*, 1982, 104, 4666) was used in place of tetrahydropyran-4-one.

The residue, containing a mixture of diastereoisomers, was purified and the isomers were separated by column chromatography using a 5:1 v/v mixture of toluene and ethyl acetate as eluent. There were thus obtained (2RS,4SR)-4-(3-benzyloxy-5-fluorophenyl)-4-hydroxy-2-methyltetrahydropyran (24%) as an oil, i.e. the 2-methyl and 4-hydroxy substituents are in a trans relationship;

NMR Spectrum: (CDCl$_3$, delta values) 1.20 (d, 3H), 1.58 (broad s, 1H, OH), 1.52 (s, 2H), 1.99–2.14 (m, 1H), 3.86–4.02 (m, 3H), 5.05 (s, 2H), 6.60 (doublet of triplets, 1H), 6.80 (doublet of triplets, 1H), 6.90 (s, 1H), 7.28–7.48 (m, 5H, aromatic); and (2SR,4SR)-4-(3-benzyloxy-5-fluorophenyl)-4-hydroxy-2-methyltetrahydropyran (48%), m.p. 82°–83° C., i.e. the 2-methyl and 4-hydroxy substituents are in a cis relationship;

NMR Spectrum: (CDCl$_3$, delta values) 1.21 (t, 3H), 1.66 (doublet of doublets, 1H), 1.80 (broad s, 1H, OH), 1.96 (triplet of doublets, 1H), 2.23–2.35 (m, 2H), 3.30–3.42 (m, 2H), 3.94 (doublet of quartets, 1H), 5.05 (s, 2H), 6.64 (doublet of triplets, 1H), 6.79 (doublet of triplets, 1H), 6.87 (s, 1H), 7.30–7.42 (m, 5H, aromatic).

The (2RS,4SR)-isomer was methylated and the benzyl protecting group was hydrogenolysed using the procedures described in the last two paragraphs of Note c. below Table I in Example 2. There was thus obtained the required starting material (61%), m.p. 127° C.

EXAMPLE 5

The procedure described in Example 4 was repeated except that the other diastereoisomer, namely (2SR,4SR)-4-(5-fluoro-3-hydroxyphenyl)-4-methoxy-2-methyltetrahydropyran was used. There was thus obtained (2SR,4SR)-4-[5-fluoro-3-(quinoxalin-6-ylmethoxy)phenyl]-4-methoxy-2-methyltetrahydropyran, as an oil (72%).

NMR Spectrum: (CDCl$_3$, delta values) 1.20 (d, 3H), 1.64 (doublet of doublets, 1H), 1.94 (triplet of doublets, 1H), 2.22–2.39(m, 2H), 2.90 (s, 3H), 3.31–3.48 (m, 2H), 3.91–4.02 (m, 1H), 5.32 (s, 2H), 6.70 (doublet of triplets, 1H), 6.79 (doublet of triplets, 1H), 6.90 (t, 1H), 7.87 (doublet of doublets, 1H), 8.17 (m, 2H), 8.89 (s, 2H);

Mass Spectrum: P m/e 382;

Elemental Analysis: Found C, 70.0; H, 6.3; N, 6.7; C$_{22}$H$_{23}$FN$_2$O$_3$. 0.25 CH$_3$-C$_6$H$_5$ requires C, 70.3; H, 6.2; N, 6.9%.

The (2SR,4SR)-4-(5-fluoro-3-hydroxyphenyl)-4-methoxy-2-methyltetrahydropyran, used as a starting material, was obtained from (2SR,4SR)-4-(3-benzyloxy-5-fluorophenyl)-4-hydroxy-2-methyltetrahydropyran, described in the portion of Example 4 which is concerned with the preparation of starting materials by the steps of methylation and subsequent hydrogenolysis of the benzyl protecting group using the procedures described in the last two paragraphs of Note c. below Table I in Example 2. There was thus obtained the required starting material (71%), m.p. 116° C.

EXAMPLE 6

Using the procedure described in Example 1, the appropriate alkyl halide was reacted with the appropriate phenol to give the compounds described in the following table:

TABLE II

Q—CH$_2$—O—Ar, OR$^1$ (tetrahydropyran ring)

| Ex. 6 Compd. No. | Q | Ar | R$^1$ | Yield (%) | m.p. (°C.) |
|---|---|---|---|---|---|
| 1$^a$ | 1,2-dihydro-1-methyl-2-oxoquinolin-6-yl | 1,3-phenylene | Me | 74 | 97–99 |
| 2$^b$ | 1,2-dihydro-1-methyl-2-oxoquinolin-6-yl | 1,3-phenylene | Et | 52 | 131–132 |
| 3$^c$ | 1,2-dihydro-1-methyl-2-oxoquinolin-5-yl | 1,3-phenylene | Me | 59 | 112–113 |
| 4$^d$ | 1,2-dihydro-1-methyl-2-oxoquinolin-7-yl | 1,3-phenylene | Me | 64 | 74–76 |
| 5$^e$ | 6-quinoxalinyl | 5-fluoro-1,3-phenylene | Et | 51 | oil |
| 6$^f$ | 6-quinolyl | 5-fluoro-1,3-phenylene | Me | 53 | 94–95 |
| 7$^g$ | 3-isoquinolyl | 5-fluoro-1,3-phenylene | Me | 73 | 80–81 |
| 8$^h$ | 2-quinazolinyl | 5-fluoro-1,3-phenylene | Me | 77 | foam |
| 9$^i$ | 6-quinazolinyl | 5-fluoro-1,3-phenylene | Me | 79 | 126–128 |
| 10$^j$ | 1,2-dihydro-1-methyl-2-oxoquinolin-3-yl | 5-fluoro-1,3-phenylene | Et | 75 | 88–89 |
| 11$^k$ | 1,2-dihydro-6-fluoro-1-methyl-2-oxoquinolin-3-yl | 5-fluoro-1,3-phenylene | Me | 52 | 154–155 |
| 12$^l$ | 1,2-dihydro-1-ethyl-2-oxoquinolin-3-yl | 5-fluoro-1,3-phenylene | Me | 49 | 97–98 |
| 13$^m$ | 1,2-dihydro-1-(2-fluoroethyl)-2-oxoquinolin-3-yl | 5-fluoro-1,3-phenylene | Me | 55 | 125–126 |
| 14$^n$ | 1,2-dihydro-1-(2-dimethylaminoethyl)-2-oxoquinolin-3-yl | 5-fluoro-1,3-phenylene | Me | 50 | 88–90 |
| 15$^o$ | 1,2-dihydro-2-oxoquinolin-6-yl | 5-fluoro-1,3-phenylene | Me | 82 | 220 |
| 16 | 1,2-dihydro-1-methyl-2-oxoquinolin-6-yl | 5-fluoro-1,3-phenylene | Me | 88 | 147 |
| 17$^p$ | 1,2-dihydro-1-(2-fluoroethyl)-2-oxoquinolin-6-yl | 5-fluoro-1,3-phenylene | Me | 32 | 143–144 |
| 18$^q$ | 1,2-dihydro-1-benzyl-2-oxoquinolin-6-yl | 5-fluoro-1,3-phenylene | Me | 74 | gum |
| 19$^r$ | 1,2-dihydro-1-methyl-2-oxoquinolin-6-yl | 2,5-difluoro-1,3-phenylene | Me | 73 | 124–126 |
| 20$^s$ | 6-quinoxalinyl | 5-trifluoromethyl-1,3-phenylene | Me | 70 | oil |
| 21$^t$ | 6-quinoxalinyl | 5-trifluoro- | Et | 82 | oil |

TABLE II-continued

Q—CH₂—O—Ar⟨OR¹ (tetrahydropyran ring with O)

| Ex. 6 Compd. No. | Q | Ar | R¹ | Yield (%) | m.p. (°C.) |
|---|---|---|---|---|---|
| 22[u] | 6-quinoxalinyl | methyl-1,3-phenylene 3,5-pyridylene | Me | 78 | 98–99 |
| 23[v] | 6-quinoxalinyl | 5-cyanomethoxy-1,3-phenylene | Me | 86 | oil |

Notes a. The 6-bromomethyl-1,2-dihydro-1-methylquinolin-2-one, used as a starting material, was obtained as follows:

A mixture of 1,2-dihydro-1,6-dimethylquinolin-2-one (4.4 g; *Helv. Chim. Acta.*, 1970, 53, 1903), N-bromosuccinimide (4.53 g), azobisisobutyronitrile (0.01 g) and carbon tetrachloride (75 ml) was heated to reflux for 3 hours. The mixture was evaporated and the residue was partitioned between ethyl acetate and water. The organic phase was washed with water, dried (MgSO₄) and evaporated. The residue was purified by column chromatography using a 2:1 v/v mixture of toluene and ethyl acetate as eluent. There was thus obtained the required starting material (4.8 g, 75%), as a solid, m.p. 107°–108° C.

NMR Spectrum (CDCl₃, delta values) 3.7(s, 3H), 4.57(s, 2H), 6.7–7.5(d, 1H), 7.25–7.65(m, 4H).

b. The 4-ethoxy-4-(3-hydroxyphenyl)tetrahydropyran, used as a starting material, was obtained as follows:

A Grignard reagent was prepared by heating a mixture of 3-(naphth-2-ylmethoxy)bromobenzene (3 g), magnesium powder (0.23 g) and tetrahydrofuran (12 ml) to 30° C. for 1.5 hours. The reagent was cooled to 20° C. and a solution of tetrahydropyran-4-one (0.88 ml) in tetrahydropyran (5 ml) was added dropwise. The mixture was heated to 30° C. for 15 hours, evaporated and the residue was partitioned between ethyl acetate and water. The organic layer was separated, washed with a saturated aqueous sodium chloride solution, dried (MgSO₄) and evaporated. The residue was purified by column chromatography using a 7:3 v/v mixture of methylene chloride and diethyl ether as eluent. There was thus obtained 4-hydroxy-4-[3-(naphth-2-ylmethoxy)phenyl]tetrahydropyran (2.06 g, 42%), m.p. 130°–131° C.

A mixture of a portion (0.68 g) of the product so obtained, sodium hydride (60% w/w dispersion in mineral oil; 0.1 g), 15-crown-5 (0.01 g), ethyl iodide (0.325 ml) and dimethylformamide (5 ml) was stirred at ambient temperature for 48 hours. The mixture was partitioned between diethyl ether and water. The organic phase was washed with a saturated aqueous sodium chloride solution, dried (MgSO₄) and evaporated. The residue was purified by column chromatography using a 49:1 v/v mixture of methylene chloride and diethyl ether as eluent. There was thus obtained 4-ethoxy-4-[3-(naphth-2-ylmethoxy)phenyl]tetrahydropyran (0.5 g, 60%), as an oil.

A mixture of a portion (0.4 g) of the product so obtained, 10% palladium-on-charcoal catalyst (0.08 g) and ethanol (25 ml) was stirred under a pressure of 3.3 atmospheres of hydrogen gas for 15 hours. The mixture was filtered and the filtrate was evaporated. The residue was purified by column chromatography using a 1:1 v/v mixture of methylene chloride and diethyl ether as eluent. There was thus obtained the required starting material (0.175 g, 87%), m.p. 124°–126° C.

c. The 5-bromomethyl-1,2-dihydro-1-methylquinolin-2-one, used as a starting material, was obtained as follows:

1,2-Dihydro-5-methylquinolin-2-one (1.59 g; *Synthesis*, 1975, 739) was added to a stirred suspension of sodium hydride (55% w/w dispersion in mineral oil, 0.264 g) in dimethylformamide (40 ml) and the mixture was heated to 50° C. for 45 minutes. The mixture was cooled to 0° C. and methyl iodide (0.93 ml) was added dropwise. The mixture was stirred at ambient temperature for 16 hours. The mixture was evaporated and the residue was partitioned between ethyl acetate and water. The organic phase was washed with a saturated aqueous sodium chloride solution, dried (MgSO₄) and evaporated. The residue was purified by column chromatography using a 19:1 v/v mixture of methylene chloride and methanol as eluent. There was thus obtained 1,2-dihydro-1,5-dimethylquinolin-2-one (1.5 g, 87%), m.p. 107°–108° C.

A mixture of a portion (1.21 g) of the product so obtained, N-bromosuccinimide (1.37 g), benzoyl peroxide (0.035 g) and carbon tetrachloride (25 ml) was heated to reflux for 40 minutes and irradiated with the light from a 275 watt lamp. The mixture was evaporated and the residue was partitioned between ethyl acetate and water. The organic phase was washed with a saturated aqueous sodium chloride solution, dried (MgSO₄) and evaporated. The residue was purified by column chromatography using in turn methylene chloride and then a 4:1 v/v mixture of toluene and ethyl acetate as eluent. There was thus obtained the required starting material (1.09 g, 59%) m.p. 169° C.

d. The 7-bromomethyl-1,2-dihydro-1-methylquinolin-2-one, used as a starting material, was obtained using the following procedure:

1,2-Dihydro-7-methylquinolin-2-one (*Synthesis*, 1975, 739) was reacted with methyl iodide using the procedure described in Note c. immediately above. There was thus obtained 1,2-dihydro-1,7-dimethylquinolin-2-one in 79% yield, m.p. 111°–112° C.

The product so obtained was brominated using the procedure described in Note c. immediately above to give the required starting material in 57% yield, m.p. 170° C.

e. The product displayed the following characteristic NMR signals (CDCl₃, delta values) 1.1(t, 3H), 1.9-2.1(m, 4H), 3.1(q, 2H), 3.75-3.95(m, 4H), 5.3(s, 2H), 6.62-6.9(m, 3H), 7.85(d, 1H), 8.15(d, 2H), 8.85(s, 2H).

f. Three equivalents of potassium carbonate were used. 6-Chloromethylquinoline hydrochloride, used as a starting material, was prepared as follows:

A mixture of 4-aminobenzoic acid (27.5 g), 4-nitrobenzoic acid (21.3 g), ferrous sulphate (7 g), boric acid (12 g), glycerol (75 ml) and concentrated sulphuric acid (35 ml) was heated to reflux for 20 hours. The mixture was diluted with water (200 ml) and basified by adding a 5N aqueous sodium hydroxide solution. The mixture was filtered and the filtrate was acidified to pH 4-5 by adding glacial acetic acid. The mixture was stored at 0° C. for 2 hours. The precipitate was isolated by filtration, washed with water and with acetone, and dried by heating to 55° C. in vacuo. There was thus obtained quinolin-6-carboxylic acid (78 g), m.p. 286° C.

A mixture of the product so obtained, ethanol (600 ml) and concentrated sulphuric acid (96 ml) was heated to reflux for 5 hours. The bulk of the ethanol was evaporated. Water (200 ml) was added and the mixture was basified by adding a 5N aqueous sodium hydroxide solution. The mixture was extracted with chloroform (3×100 ml). The combined extracts were dried ($Na_2SO_4$) and evaporated. There was thus obtained ethyl quinoline-6-carboxylate (17 g, b.p. 140°-145° C. at 0.05 mm Hg).

A solution of the product so obtained in diethyl ether (100 ml) was added to a mixture of lithium aluminium hydride (3.6 g) and diethyl ether (200 ml) at a rate sufficient to heat the mixture to a gentle reflux. The mixture was then heated to reflux for 20 minutes. Wet ether (100 ml) was added carefully and then aqueous sodium hydroxide solution [4.6 g in water (30 ml)] was added. The mixture was filtered and the solid was washed with diethyl ether. The combined filtrate and washings were washed with a saturated aqueous sodium chloride solution, dried ($Na_2SO_4$) and evaporated. There was thus obtained 6-hydroxymethylquinoline [7 g, recrystallised from a mixture of petroleum ether (b.p. 60°-80° C.) and diethyl ether].

A saturated solution of hydrogen chloride in diethyl ether was added to a solution of the product so obtained in methanol (25 ml) which had been cooled in an ice-bath. The precipitate of 6-hydroxymethylquinoline hydrochloride so formed was filtered off and washed with diethyl ether. A mixture of the product so obtained and thionyl chloride was heated to reflux for 3 hours. The mixture was evaporated, toluene was added and the mixture was re-evaporated. The residue was triturated in diethyl ether to give 6chloromethylquinoline hydrochloride.

g. Three equivalents of potassium carbonate were used. 3-Chloromethylisoquinoline hydrochloride, used as a starting material, was obtained as follows:

A mixture of phenylaniline (40 g), formaldehyde (37% w/v in water, 91 ml) and concentrated hydrochloric acid (310 ml) was stirred and heated to reflux for 4 hours and then stored at ambient temperature for 16 hours. The precipitate was filtered off, washed with cold water and with acetone to give 1,2,3,4-tetrahydroisoquinoline-3-carboxylic acid (11 g).

After appropriate repetition of the above step a mixture of the product so obtained (23.2 g) and methanol (200 ml) was cooled in an ice-bath and thionyl chloride (15.4 ml) was added dropwise. The mixture was heated to reflux for 4 hours. The mixture was evaporated and the solid residue was triturated in diethyl ether to give ethyl 1,2,3,4-tetrahydroisoquinoline-3-carboxylate hydrochloride (23.2 g).

NMR Spectrum: ($CD_3SOCD_3$, delta values) 3.1-3.4(m, 2H), 3.8(s, 3H), 4.32(s, 2H), 4.5-4.6(q, 1H), 7.3(s, 4H), 10.2(broad s, 1H).

A mixture of a portion (11 g) of the product so obtained, potassium acetate (19.6 g) and dry ethanol (200 ml) was heated to reflux and a solution of iodine (25.4 g) in dry ethanol (250 ml) was added over a period of 3 hours to the heated mixture. The mixture was heated to reflux for 16 hours, cooled and filtered and the filtrate was evaporated. The residue was partitioned between ethyl acetate and a dilute aqueous sodium thiosulphate solution. The organic layer was dried ($Na_2SO_4$) and evaporated. The residue was purified by column chromatography eluting with ethyl acetate to give ethyl isoquinoline-3-carboxylate (3 g).

Using the procedure described in the last two paragraphs of Note f. immediately above, the product so obtained was reduced and the resultant alcohol was converted into the required starting material.

h. 2-Chloromethylquinazoline, used as the alkylating agent, is described in *J. Chem. Soc.*, 1966, 238. The product displayed the following characteristic NMR signals ($CDCl_3$, delta values) 1.75-2.03(m, 4H), 2.93(s, 3H), 3.71-3.91(m, 4H), 5.46(s, 2H), 6.69(d, 1H), 6.74(d, 1H), 6.95(s, 1H), 7.69(t, 1H), 7.9-8.1(m, 3H), 9.45(s, 1H).

i. 6-Bromomethylquinazoline, used as the alkylating agent, was prepared from 6-methylquinazoline (*J. Chem. Soc.*, 1962, 561) using the procedure described in *J. Het. Chem.*, 1974, 11, 595 for the preparation of 6-bromomethylquinoxaline from 6-methylquinoxaline.

j. 4-Ethoxy-4-(5-fluoro-3-hydroxyphenyl)tetrahydropyran, used as a starting material, was obtained from 4-(3-benzyloxy-5-fluorophenyl)-4-hydroxytetrahydropyran using the procedures described in Note c. below Table I in Example 2, except that ethyl iodide was used in place of methyl iodide. There was thus obtained the required starting material in 60% yield, m.p. 112° C.

k. The 3-bromomethyl-6-fluoro-1,2-dihydro-1-methylquinolin-2-one, used as a starting material, was obtained as follows:

Triethylamine (18.2 g) and propionyl chloride (16.7 g) were added in turn to a solution of 4-fluoroaniline (20 g) which had been cooled to 0° C. The mixture was stirred at 5° C. for 1 hour and partitioned between methylene chloride and water. The organic layer was washed with water, dried ($MgSO_4$) and evaporated to give 4-fluoropropionanilide (29.1 g).

Phosphorus oxychloride (50.3 ml) was added dropwise to dimethylformamide (11.2 ml) which was stirred and cooled to −5° C. As a white solid began to form the mixture was cooled to −15° C. and the phosphorus oxychloride was added more quickly. The white slurry so formed was stirred and allowed to warm to ambient temperature, and then stirred at ambient temperature for 30 minutes. A portion (15 g) of the 4-fluoropropionaldehyde obtained above was added portionwise and the mixture was heated to 75° C. for 6 hours. The mixture was poured onto ice and extracted with ethyl acetate. The organic layer was washed with a saturated aqueous sodium chloride solution, dried ($MgSO_4$) and evaporated. The residue was purified by column chromatography using toluene as eluent. There was thus obtained 2-chloro-6-fluoro-3-methylquinoline (1 g, 5%), as a solid.

NMR Spectrum: ($CDCl_3$, delta values) 2.54(s, 3H), 7.32-7.49(m, 2H), 7.91(s, 1H), 7.98(m, 1H).

After appropriate repetition of the above reaction steps, a mixture of the quinoline so obtained (10 g), 2N aqueous hydrochloric acid (110 ml) and ethanol (110 ml) was heated to 80° C. for 9 hours. The mixture was poured into water and the precipitate was filtered off and dried in vacuo at 50° C. There was thus obtained 6-fluoro-1,2-dihydro-1-methylquinolin-2-one (7.9 g, 87%).

NMR Spectrum: (CDCl$_3$, delta values) 2.3(s, 3H), 7.18(d, 1H), 7.2(m, 1H), 7.4(d of d's, 1H), 7.6(s, 1H), 12.3(broad hump, 1H).

Sodium hydride (55% w/w dispersion in mineral oil; 0.775 g) was added portionwise to a solution of a portion (3 g) of the product so obtained in dimethylformamide (80 ml) which had been cooled to 0° C. and the mixture was stirred at 5° C. for 40 minutes. Methyl iodide (2.65 g) was added dropwise and the mixture was stirred at 5° C. for 1 hour and then allowed to warm to ambient temperature. The mixture was poured into water (100 ml) and the precipitate was filtered off and dried in vacuo at 50° C. There was thus obtained 6-fluoro-1,2-dihydro-1,3-dimethylquinolin-2-one (2.5 g, 78%), m.p. 132° C.

A mixture of a portion (2 g) of the product so obtained, N-bromosuccinimide (1.86 g), azobisisobutyronitrile (0.01 g) and carbon tetrachloride (50 ml) was heated to reflux for 1.5 hours and illuminated with the light from a 275 watt lamp. The mixture was evaporated and the residue was partitioned between methylene chloride and water. The organic phase was washed with water, dried (MgSO$_4$) and evaporated. The residue was triturated in toluene to give the required starting material (2 g, 71%), m.p. 212° C.

l. The 3-bromomethyl-1-ethyl-1,2-dihydroquinolin-2-one, used as a starting material, was obtained as follows:

The procedure described in the first two paragraphs of Note k. immediately above was repeated except that aniline was used in place of 4-fluoroaniline. There was thus obtained 2-chloro-3-methylquinoline in 63% yield, m.p. 81°–83° C.

Using the procedure described in the last three paragraphs of Note k. immediately above, except that ethyl iodide was used in place of methyl iodide, the product so obtained was converted into the required starting material in 41%, yield, as a solid.

NMR Spectrum: (CDCl$_3$, delta values) 1.39(t, 3H), 4.40(q, 2H), 4.55(s, 2H), 7.24(t, 1H), 7.37(d, 1H), 7.58(m, 2H), 7.37(s, 1H).

m. The 3-bromomethyl-1,2-dihydro-1-(2-fluoroethyl)quinolin-2-one, used as the alkylating agent, was obtained from 1,2-dihydro-3-methylquinolin-2-one using the procedures described in Note c. immediately above, except that 2-fluoroethyl bromide was used in place of methyl iodide. There was thus obtained the required starting material in 46% yield, as a solid.

NMR Spectrum: (CDCl$_3$, delta values) 4.54(s, 2H), 4.60(t, 1H), 4.70(t, 2H), 4.96(t, 1H), 7.25(t, 1H), 7.45–7.65(m, 3H), 7.90(s, 1H).

n. The 3-bromomethyl-1,2-dihydro-1-(2-dimethylaminoethyl)-quinolin-2-one hydrobromide, used as a starting material, was obtained as follows:

Sodium hydride (55% w/w dispersion in mineral oil; 2.88 g) was added portionwise to a suspension of 1,2-dihydro-2-oxoquinoline-3-carbaldehyde (5.19 g) in dimethylformamide (90 ml) and the mixture was stirred at ambient temperature for 1 hour. 2-Dimethylaminoethyl chloride hydrochloride (4.8 g) was added and the mixture was heated to 60° C. for 3 hours. The mixture was filtered and partitioned between methylene chloride and water. The organic layer was washed with water, dried (MgSO$_4$) and evaporated. The residue was purified by column chromatography using a 4:1 v/v mixture of methylene chloride and ethanol as eluent. There was thus obtained 1,2-dihydro-1-(2-dimethylaminoethyl)-2-oxoquinoline-3-carbaldehyde (1.64 g, 22%), m.p. 98°–99° C.

Sodium borohydride (0.285 g) was added portionwise to a solution of the product so obtained in methanol (35 ml) which was cooled in an ice-bath. The mixture was stirred at ambient temperature for 2 hours and then evaporated. A 2N aqueous sodium hydroxide solution (5 ml) was added, followed by sufficient drying agent (MgSO$_4$) to dry the mixture. The mixture was filtered and evaporated. There was thus obtained 1,2-dihydro-3-hydroxymethyl-1-(2-dimethylaminoethyl)quinolin-2-one (1.48 g, 92%), as a foam.

A mixture of a portion (0.74 g) of the product so obtained and concentrated hydrobromic acid (48% w/v; 10 ml) was heated to 75° C. for 4 hours. The mixture was allowed to cool to ambient temperature, ethanol (10 ml) was added and the mixture was evaporated. The process of adding ethanol and evaporating the mixture so obtained was repeated several times to remove the hydrobromic acid. There was thus obtained the required starting material (0.62 g, 53%), m.p. 233°–238° C. (decomposes).

o. The product was obtained as follows: A mixture of 4-[5-fluoro-3-(1,2-dihydro-1-(pivaloyloxymethyl)-2-oxoquinolin-6-ylmethoxy)phenyl]-4-methoxytetrahydropyran (0.53 g), 2N aqueous sodium hydroxide solution (0.59 ml) and ethanol (25 ml) was stirred at ambient temperature for 3 hours. The mixture was evaporated and the residue was partitioned between methylene chloride and water. The organic phase was washed with water, dried (MgSO$_4$) and evaporated to give 4-[5-fluoro-3-(1,2-hydro-2-oxoquinolin-6-ylmethoxy)-phenyl]-4-methoxytetrahydropyran (0.42 g, 82%), m.p. 220° C.

The starting material was obtained by the reaction of 6-bromomethyl-1,2-dihydro-1-(pivaloyloxymethyl)-quinolin-2-one with 4-(5-fluoro-3-hydroxyphenyl)-4-methoxytetrahydropyran using the procedure described in Example 1. There was thus obtained the required starting material in 30% yield, as a solid.

NMR Spectrum: (CDCl$_3$, delta values) 1.20(s, 9H), 1.85–2.07(m, 4H), 2.98(s, 3H), 3.78–3.89(m, 4H), 5.10(s, 2H), 6.33(s, 2H), 6.63(m, 1H), 6.7–6.75(m, 2H), 6.83(t, 1H), 7.35(d, 1H), 7.58–7.65(m, 2H), 7.71(d, 1H).

The 6-bromomethyl-1,2-dihydro-1-(pivaloyloxymethyl)quinolin-2-one, used as the alkylating agent, was obtained as follows:

A solution of cinnamoyl chloride (33.3 g) in methylene chloride (100 ml) was added dropwise to a stirred mixture of 4-methylaniline (21.4 g), pyridine (16.2 ml) and methylene chloride (500 ml) which had been cooled in an ice-bath. The mixture was stirred at 5° C. for 20 minutes and then allowed to warm to ambient temperature. The mixture was washed in turn with water, 1N aqueous hydrochloric acid solution, a saturated aqueous sodium bicarbonate solution and water. The organic solution was dried (MgSO$_4$) and evaporated to give N-(4-tolyl)cinnamide (46 g, 97%), as a solid.

NMR Spectrum: (CDCl$_3$, delta values) 2.32(s, 3H), 6.54(d, 1H), 7.11–7.52(m, 10H), 7.73(d, 1H).

A mixture of a portion (5.4 g) of the product so obtained and aluminum chloride (16.2 g) was heated strongly until a brown viscous liquid was formed. The mixture was then heated on a steam bath for 2 hours. The mixture was poured onto ice and the resulting solid was filtered off and washed with 2N aqueous hydrochloric acid solution and with water. The solid was dried and triturated in ethyl acetate. There was thus obtained 1,2-dihydro-6-methylquinolin-2-one (3.4 g), as a solid.

NMR Spectrum: (CD$_3$SOCD$_3$, delta values) 2.33(s, 3H), 6.44(d, 1H), 7.19(d, 1H), 7.31(d of d's, 1H), 7.42(s, 1H), 7.80(d, 1H), 11.6(broad s, 1H).

Using the procedure described in Note c. immediately above, the product so obtained was reacted with chloromethyl pivalate to give 1,2-dihydro-6-methyl-1-(pivaloyloxymethyl)quinolin-2-one in 45% yield, as a solid.

NMR Spectrum: (CDCl$_3$, delta values) 1.18(s, 9H), 2.41(s, 3H), 6.31(s, 2H), 6.65(d, 1H), 7.16–7.40(m, 3H), 7.64(d, 1H).

Using the procedure described in Note a. immediately above, the product so obtained was brominated to give the required starting material in quantitative yield, as an oil which was used without further purification.

p. The 6-bromomethyl-1,2-dihydro-1-(2-fluoroethyl)-quinolin-2-one, used as the alkylating agent, was obtained from 1,2-dihydro-6-methylquinolin-2-one using the procedures described in Note c. immediately above, except that 2-fluoroethyl bromide was used in place of methyl iodide. There was obtained the required starting material in 48% yield, as a solid.

NMR Spectrum (CDCl$_3$, delta values) 4.56(s, 2H), 4.5–4.9(m, 4H), 6.72(d, 1H), 7.3–7.8(m, 4H).

q. The product was obtained by the alkylation of 4-[5-fluoro-3-(1,2-dihydro-2-oxoquinolin-6-ylmethoxy)-phenyl]-4-methoxytetrahydropyran (Example 6, Compound No. 15) with benzyl bromide using the procedure described in Note c. above.

The product displayed the following characteristic NMR signals (CDCl$_3$, delta values) 1.80–2.01(m, 4H), 2.96(s, 3H), 3.75–3.87(m, 4H), 5.05(s, 2H), 5.57(s, 2H), 6.60(m, 1H), 6.7–6.84(m, 3H), 7.18–7.37(m, 6H), 7.49(m, 1H), 7.63(d, 1H), 7.75(d, 1H).

r. The 4-(2,5-difluoro-3-hydroxyphenyl)-4-methoxytetrahydropyran, used as a starting material, was obtained as follows:

Using the procedure described in the first paragraph of Note c. below Table I in Example 2, 1-bromo-2,3,5-trifluorobenzene was reacted with benzyl alcohol, the product so obtained was reacted with n-butyl-lithium and the resultant organometallic compound was reacted with tetrahydropyran-4-one. There was thus obtained 4-(3-benzyloxy-2,5-difluorophenyl)-4-hydroxytetrahydropyran in 16% yield, as an oil.

NMR Spectrum: (CDCl$_3$, delta values) 1.36–1.41(d, 2H), 1.80(m, 1H), 1.96–2.08(m, 2H), 3.5–3.66(m, 4H), 4.78(s, 2H), 6.32–6.38(m, 1H), 6.39–6.5(m, 1H), 7.0–7.1(m, 5H).

Using the procedures described in the third and fourth paragraphs of Note s. immediately below, the product so obtained was methylated and the benzyl group was hydrogenolysed. There was thus obtained the required starting material in 53% yield, as an oil.

NMR Spectrum (CDCl$_3$, delta values) 2.0–2.06(m, 4H), 3.0(s, 3H), 3.72–3.77(m, 4H), 6.3–6.4(m, 1H), 6.5–6.6(m, 1H), 9.38(s, 1H).

s. The product displayed the following characteristic NMR signals (CD$_3$SOCD$_3$) 1.9–2.0(m, 4H), 2.9(s, 3H), 3.6–3.8(m, 4H), 5.55(s, 2H), 7.1–7.3(m, 1H), 7.4(s, 2H), 7.9–8.3(m, 3H), 9.0(s, 2H).

The 4-(3-hydroxy-5-trifluoromethylphenyl)-4-methoxytetrahydropyran used as a starting material was obtained as follows:

Sodium hydride (55% w/w dispersion in mineral oil; 4.36 g) was added portionwise to a mixture of benzyl alcohol (9.82 ml) and dimethylacetamide (136 ml) which had been cooled in an ice-bath. The mixture was stirred at ambient temperature for 1.5 hours and then recooled in an ice-bath. A solution of 3-fluoro-5-trifluoromethylbromobenzene (22.1 g) in dimethylacetamide (136 ml) was added and the mixture was stirred at ambient temperature for 2 hours. The mixture was evaporated and the residue was partitioned between diethyl ether and water. The organic phase was washed with a saturated aqueous sodium chloride solution, dried (MgSO$_4$) and evaporated. The residue was purified by column chromatography using hexane as eluent. There was thus obtained 3-benzyloxy-5-trifluoromethylbromobenzene (23.1 g, 77%), as a colourless liquid.

NMR Spectrum: 5.07(s, 2H), 7.15–7.35(3 s's, 3H), 7.36–7.42(m, 5H).

A solution of n-butyl-lithium (25.9 ml of a 1.6M solution in hexane) was added dropwise to a solution of a portion (13.75 g) of the compound so obtained in tetrahydrofuran (150 ml) which had been cooled to −70° C. The mixture was stirred at this temperature for 1 hour. A solution of tetrahydropyran-4-one (4.15 g) in tetrahydrofuran (5 ml) was added dropwise and the mixture was stirred at −70° C. for 1 hour, and then allowed to warm to 0° C. A saturated aqueous ammonium chloride solution (100 ml) was added and the mixture was extracted with diethyl ether. The organic phase was washed with a saturated aqueous sodium chloride solution, dried (MgSO$_4$) and evaporated. The residue was purified by column chromatography using a 4:1 v/v mixture of toluene and ethyl acetate as eluent. There was thus obtained 4-(3-benzyloxy-5-trifluoromethylphenyl)-4-hydroxytetrahydropyran (11.5 g, 79%), as a solid.

NMR Spectrum: (CDCl$_3$, delta values) 1.6–1.72(m, 2H), 2.05–2.25(m, 2H), 3.6–4.0(m, 4H), 5.12(s, 2H), 7.1–7.5(m, 8H).

Sodium hydride (55% w/w dispersion in mineral oil, 0.262 g) was added to a mixture of a portion (1.92 g) of the product so obtained and dimethylformamide (12 ml) which had been cooled to −5° C. The mixture was stirred at −5° C. for 30 minutes. Methyl iodide (0.38 ml) was added dropwise and the mixture was stirred at ambient temperature for 90 minutes. The mixture was poured onto ice and extracted with diethyl ether. The organic phase was washed with water, dried (MgSO$_4$) and evaporated. The residue was purified by column chromatography using a 10:1 v/v mixture of toluene and ethyl acetate as eluent. There was thus obtained 4-(3-benzyloxy-5-trifluoromethylphenyl)-4-methoxytetrahydropyran (1.76 g, 88%), as an oil.

NMR Spectrum: (CDCl$_3$, delta values) 1.9–2.1(m, 4H), 3.0(s, 3H), 3.8–3.9(m, 4H), 5.1(s, 2H), 7.0–7.5(m, 8H).

A mixture of the product so obtained, 10% palladium-on-charcoal catalyst (0.32 g) and isopropanol (25 ml) was stirred under an atmosphere of hydrogen for 2 hours. The mixture was filtered and the filtrate was evaporated to give the required starting material (1.14 g, 89%), m.p. 132°-134° C.

NMR Spectrum: (CDCl$_3$, delta values) 1.9-2.1(m, 4H), 3.0(s, 3H), 3.8-4.0(m, 4H), 5.95(s, 1H), 7.0(m, 1H), 7.1(m, 1H), 7.2(s, 1H).

t. The product displayed the following characteristic NMR signals (CD$_3$SOCD$_3$, delta values) 0.9-1.1(t, 3H), 1.8-2.0(m, 4H), 2.9-3.1(q, 2H), 3.6-3.8(m, 4H), 5.5(s, 2H), 7.1-7.4(m, 3H), 7.9-8.0(m, 1H), 8.1-8.2(m, 1H), 8.2(m, 1H), 8.5(s, 2H).

The 4-ethoxy-4-(3-hydroxy-5-trifluoromethylphenyl)tetrahydropyran, used as a starting material, was obtained as follows:

Powdered potassium hydroxide (1.5 g) was added to a solution of 4-(3-benzyloxy-5-trifluoromethylphenyl)-4-hydroxytetrahydropyran (2.17 g) in dimethylsulphoxide (15 ml) and the mixture was stirred at ambient temperature for 10 minutes. Ethyl iodide (1.24 ml) was added and the mixture was stirred at ambient temperature for 4 hours. The mixture was poured onto a mixture of diethyl ether and ice. The organic phase was separated, washed with water, dried (MgSO$_4$) and evaporated. The residue was purified by column chromatography using a 10:1 v/v mixture of toluene and ethyl acetate as eluent. There was thus obtained 4-(3-benzyloxy-5-trifluoromethylphenyl)-4-ethoxytetrahydropyran (1.75 g, 74%), as an oil.

NMR Spectrum: (CDCl$_3$, delta values) 1.1-1.2(t, 3H), 1.8-2.1(m, 4H), 3.0-3.1(q, 2H), 3.75-3.95(m, 4H), 5.1(s, 2H), 7.1-7.5(m, 8H).

A mixture of the product so obtained, 10% palladium-on-charcoal catalyst (0.35 g) and isopropanol (25 ml) was stirred under an atmosphere of hydrogen for 3.5 hours. The mixture was filtered and evaporated. There was thus obtained the required starting material (1.3 g, 97%), as an oil.

NMR Spectrum: (CDCl$_3$, delta values) 1.1-1.2(t, 3H), 1.9-2.1(m, 4H), 3.05-3.15(q, 2H), 3.8-4.0(m, 4H), 7.0(m, 1H), 7.1(m, 1H), 7.2(s, 1H).

u. The alkylation reaction was carried out at −20° C. rather than at ambient temperature and using sodium hydride (55% w/w dispersion in mineral oil) rather than potassium carbonate as the base.

v. The product displayed the following characteristic NMR signals: (CDCl$_3$, delta values) 1.75-2.25(m, 4H), 3.0(s, 3H), 3.6-4.0(m, 4H), 4.75(s, 2H), 5.30(s, 2H), 6.5-6.85(m, 3H), 7.75-7.95(m, 1H), 8.0-8.25(m, 2H), 8.85(m, 2H).

EXAMPLE 7

Using the procedure described in Example 1, the appropriate alkyl halide was reacted with the appropriate phenol to give the compounds described in the following table:

TABLE III

Q—CH$_2$—O—Ar—OR$^1$ (with R substituent on tetrahydropyran ring)

| Ex. 7 Compd No. | Q | Ar | R$^1$ | R | Yield (%) | m.p. (°C.) |
|---|---|---|---|---|---|---|
| 1$^a$ | 1,2-dihydro-1-methyl-2-oxoquinolin-6-yl | 5-fluoro-1,3-phenylene | Me | alpha-Me | 54 | foam |
| 2$^b$ | 1,2-dihydro-1-methyl-2-oxoquinolin-6-yl | 5-fluoro-1,3-phenylene | Me | beta-Me | 41 | oil |
| 3$^c$ | 1,2-dihydro-1-ethyl-2-oxoquinolin-6-yl | 5-fluoro-1,3-phenylene | Me | alpha-Me | 50 | oil |
| 4$^d$ | 1,2-dihydro-1-ethyl-2-oxoquinolin-6-yl | 5-fluoro-1,3-phenylene | Me | beta-Me | 73 | foam |
| 5 | 1,2-dihydro-1-methyl-2-oxoquinolin-3-yl | 5-fluoro-1,3-phenylene | Me | alpha-Me | 73 | 121-122 |
| 6$^e$ | 1,2-dihydro-1-methyl-2-oxoquinolin-6-yl | 5-amino-1,3-phenylene | Me | alpha-Me | 39 | foam |
| 7$^f$ | 1,2-dihydro-1-methyl-2-oxoquinolin-6-yl | 5-ureido-1,3-phenylene | Me | alpha-Me | 70 | 191 |

Notes a. (2RS,4SR)-4-(5-Fluoro-3-hydroxyphenyl)-4-methoxy-2-methyltetrahydropyran, having the 2-methyl and 4-methoxy groups in a trans-relationship, was used as the appropriate phenol.

The product displayed the following characteristic NMR signals (CDCl$_3$, delta values) 0.97(d, 3H), 1.32(d of d's, 1H), 1.63-1.80(m, 3H), 2.75(s, 3H), 3.51(s, 3H), 3.57-3.73(m, 3H), 4.88(s, 2H), 6.40(m, 1H), 6.5-6.62(m, 3H), 7.15-7.5(m, 4H).

b. (2SR,4SR)-4-(5-Fluoro-3-hydroxyphenyl)-4-methoxy-2-methyltetrahydropyran, having the 2-methyl and 4-methoxy groups in a cis-relationship, was used as the appropriate phenol.

The product displayed the following characteristic NMR signals (CDCl$_3$, delta values) 1.19(d, 3H), 1.61(d of d's, 1H), 1.96(m, 1H), 2.2-2.34(m, 2H), 2.88(s, 3H), 3.32-3.49(m, 2H), 3.72(s, 3H), 3.97(m, 1H), 5.10(s, 2H), 6.66(m, 1H), 6.7-6.8(m, 2H), 6.83(t, 1H), 7.39(d, 1H), 7.6-7.7(m, 3H).

c. The product displayed the following characteristic NMR signals (CDCl$_3$, delta values) 0.97(d, 3H), 1.14(t, 3H), 1.32(d of d's, 1H), 1.60-1.80(m, 3H), 2.75(s, 3H), 3.56-3.73(m, 3H), 4.15(q, 2H), 4.87(s, 2H), 6.39(m, 1H), 6.51(m, 1H), 6.52(d, 1H), 6.59(t, 1H), 7.19(d, 1H), 7.35-7.48(m, 3H).

The 6-bromomethyl-1,2-dihydro-1-ethylquinolin-2-one, used as a starting material, was obtained from 1,2-dihydro-6-methylquinolin-2-one using the procedures described in Note c. below Table II in Example 6, except that ethyl iodide was used in place of methyl iodide. There was thus obtained the required starting material in 21% yield, as an oil.

NMR Spectrum: (CDCl$_3$, delta values) 1.38(t, 3H), 4.35 (q, 2H), 4.57(s, 2H), 6.72(d, 1H), 7.63(d, 1H), 7.1-7.6(m, 3H).

d. The product displayed the following characteristic NMR signals (CDCl$_3$, delta values) 1.20(d, 3H), 1.37(t, 3H), 1.62(d of d's, 1H), 1.92(m, 1H), 2.21–2.38(m, 2H), 2.90(s, 3H), 3.3–3.5(m, 2H), 3.96(m, 1H), 4.37(q, 2H), 5.10(s, 2H), 6.65–6.85(m, 4H), 7.38–7.48(m, 1H), 7.59–7.72(m, 3H).

e. The product displayed the following characteristic NMR signals (CD$_3$SOCD$_3$/CF$_3$CO$_2$D/CD$_3$CO$_2$D) 1.0(d, 3H), 1.1–2.25(m, 4H), 2.9(s, 3H), 3.65(s, 3H), 3.6–4.0(m, 3H), 5.25(s, 2H), 6.65(d, 1H), 6.9–7.2(m, 3H), 7.45–8.05(m, 4H), (2RS,4SR)-4-(5-(N-benzylideneamino)-3-hydroxyphenyl)-4-methoxy-2-methyltetrahydropyran was used as the phenolic starting material and the product so obtained was stirred with 2N aqueous hydrochloric acid at ambient temperature for 12 hours. The mixture was neutralised by the addition of 2N aqueous sodium hydroxide solution and extracted with diethyl ether. The organic phase was washed with water, dried (MgSO$_4$) and evaporated. The residue was purified by column chromatography using ethyl acetate as eluent. There was thus obtained the required product in 39% yield.

The (2RS,4SR)-4-(5-(N-benzylideneamino)-3-hydroxyphenyl)-4-methoxy-2-methyltetrahydropyran starting material was obtained as follows:

Using the procedure described in the first paragraph of Note c. below Table I in Example 2, benzyl alcohol was reacted with 3,5-dinitroiodobenzene to give 3-benzyloxy-5-nitroiodobenzene in 54% yield, m.p. 79°–80° C.

Using a similar procedure to that described in Note c. below Table I in Example 2 except that the reaction was carried out at −110° C., the product so obtained was reacted with n-butyl-lithium and the organometallic reagent so formed was reacted with 2-methyltetrahydropyran-4-one [reaction mixture stirred at −100° C. for 30 minutes and then allowed to warm to ambient temperature] to give 4-(3-benzyloxy-5-nitrophenyl)-4-hydroxy-2-methyltetrahydropyran, as a mixture of diastereoisomers. The mixture of isomers so formed was separated by chromatography using a 4:1 v/v mixture of diethyl ether and petroleum ether (b.p. 40°–60° C.) as eluent. Each isomer was methylated using the conditions described in that Note. There were thus obtained a less polar diastereoisomer, (2RS,4SR)-4-(3-benzyloxy-5-nitrophenyl)-4-methoxy-2-methyltetrahydropyran in 16% yield from 3-benzyloxy-5-nitroiodobenzene, m.p. 85°–86° C.; and a more polar diastereoisomer, the (2RS,4RS)-isomer, in 22% yield, m.p. 106°–107° C.

A mixture of the less polar isomer so obtained (1.5 g), 5% palladium-on-charcoal catalyst (0.3 g) and ethanol (25 ml) was stirred under an atmosphere of hydrogen for 2 hours. The mixture was filtered and the filtrate was evaporated. The residue was purified by column chromatography using a 1:1 v/v mixture of toluene and ethyl acetate as eluent. There was thus obtained (2RS,4SR)-4-(5-amino-3-hydroxyphenyl)-4-methoxy-2-methyltetrahydropyran (0.83 g, 84%), as an oil.

NMR Spectrum (CDCl$_3$, delta values) 1.2(d, 3H), 1.4–2.2(m, 4H), 3.0(s, 3H), 3.25–4.1(m, 6H), 6.1–6.40(m, 3H).

A mixture of the product so obtained (0.8 g), benzaldehyde (0.55 g), magnesium sulphate (1 g) and methylene chloride (10 ml) was stirred at ambient temperature for 12 hours. The mixture was filtered and the filtrate was evaporated. There was thus obtained the required starting material in quantitative yield, as an oil.

f. This product was obtained by reaction of the preceding product with sodium cyanate as follows:

Sodium cyanate (0.085 g) was added portionwise to a mixture of (2RS,4SR)-4-[5-amino-3-(1,2-dihydro-1-methyl-2-oxoquinolin-6-ylmethoxy)phenyl]-4-methoxy-2-methyltetrahydropyran (0.23 g), 2N aqueous hydrochloric acid (0.5 ml), water (3 ml) and ethanol (2 ml) and the mixture was stirred at ambient temperature for 12 hours. The mixture was evaporated and the residue was partitioned between ethyl acetate and water. The organic phase was dried (MgSO$_4$) and evaporated and the residue was triturated in methylene chloride. There was thus obtained the required product in 70% yield.

EXAMPLE 8

Using the procedure described in Example 1, 6-bromomethyl-1,2-dihydro-1-methylquinolin-2-one was reacted with 4-(3-hydroxyphenyl)-4-methoxy-2,2-dimethyltetrahydropyran to give 4-[3-(1,2-dihydro-1-methyl-2-oxoquinolin-6-ylmethoxy)phenyl]-4-methoxy-2,2-dimethyltetrahydropyran in 83% yield.

NMR Spectrum: (CDCl$_3$, delta values) 1.2(s, 3H), 1.49(s, 3H), 1.75(d, 1H), 1.9–2.1(m, 3H), 2.95(s, 3H), 3.69–3.79(m, 4H), 3.99–4.11(m, 1H), 5.12(s, 2H), 6.7–6.8(d, 1H), 6.89–7.1(m, 3H), 7.1–7.5(m, 2H), 7.6–7.8(m, 3H).

The 4-(3-hydroxyphenyl)-4-methoxy-2,2-dimethyltetrahydropyran, used as a starting material, was obtained as follows:

A mixture of 2,3-dihydro-2,2-dimethylpyran-4-one (2.72 g, *J. Org. Chem.*, 1963, 687), 10% palladium-on-charcoal catalyst (0.27 g) and ethanol (80 ml) was stirred under an atmosphere of hydrogen for 6 hours. The mixture was filtered and the filtrate was evaporated. There was thus obtained 2,2-dimethyltetrahydropyran-4-one (2.05 g, 74%), as a liquid. (IR Spectrum 1730 cm$^{-1}$).

Using the procedure described in the second paragraph of Note c. below Table I in Example 2, 3-benzyloxybromobenzene (1.34 g) was reacted with 2,2-dimethyltetrahydropyran-4-one (0.65 g) to give 4-(3-benzyloxyphenyl)-4-hydroxy-2,2-dimethyltetrahydropyran (1.14 g, 72%), as an oil.

Using the procedure described in the second paragraph of the portion of Note s. below Table II in Example 6 which is concerned with the preparation of starting materials, the product so obtained was reacted with methyl iodide to give 4-(3-benzyloxyphenyl)-4-methoxy-2,2-dimethyltetrahydropyran (1.06 g, 89%), as an oil.

NMR Spectrum (CDCl$_3$, delta values) 1.18(s, 3H), 1.45(s, 3H), 1.71(d, 1H), 1.93–2.03(m, 3H), 2.92(s, 3H), 3.66–3.77(m, 1H), 3.94–4.10(m, 1H), 5.07(s, 2H), 6.88(d, 1H), 6.97(d, 1H), 7.02(s, 1H), 7.15–7.46(m, 6H).

A mixture of the product so obtained, 10% palladium-on-charcoal catalyst (0.44 g) and isopropanol (45 ml) was stirred under an atmosphere of hydrogen for 3 hours. The mixture was filtered and the filtrate was evaporated to give the required starting material (0.74 g, 96%) which was used without further purification.

EXAMPLE 9

Using the procedure described in Example 1, 3-(2-pyridyl)prop-2-yn-1-yl bromide hydrobromide was reacted with (2RS,3SR)-3-(3-hydroxyphenyl)-3-methoxy-2-methyltetrahydrofuran to give (2RS,3SR)-3-methoxy-2-methyl-3-[3-(3-(2-pyridyl)prop-2-yn-1-yloxy)phenyl]tetrahydrofuran, as an oil in 90% yield.

NMR Spectrum: (CDCl₃, delta values) 1.19(d, 3H), 2.49(t, 2H), 3.18(s, 3H), 3.72(q, 1H), 4.08(m, 2H), 4.95(s, 2H), 6.85–7.5(m, 8H).

The (2RS,3SR)-3-(3-hydroxyphenyl)-3-methoxy-2-methyltetrahydrofuran, used as a starting material, was obtained as follows:

The procedure described in the portion of Example 1 which is concerned with the preparation of starting materials was repeated except that 2-methyltetrahydrofuran-3-one was used in place of tetrahydrofuran-4-one. There was thus obtained the required starting material in 54% yield, m.p. 170°–171° C.; the 2-methyl and 3-methoxy groups being in a cis-relationship.

EXAMPLE 10

Using the procedure described in Example 1, the appropriate alkyl bromide was reacted with the appropriate phenol to give the compounds described in the following table:

TABLE IV

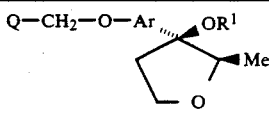

| Ex. 10 Compd. No. | Q | Ar | R¹ | Yield (%) | m.p. (°C.) |
|---|---|---|---|---|---|
| 1 | 6-quinoxalinyl | 1,3-phenylene | Me | 82 | 89–90 |
| 2 | 1,2-dihydro-1-methyl-2-oxoquinolin-6-yl | 1,3-phenylene | Me | 75 | 120 |
| 3 | 1,2-dihydro-1-methyl-2-oxoquinolin-5-yl | 1,3-phenylene | Me | 65 | 43–53 |
| 4ᵃ | 1,2-dihydro-1-methyl-2-oxoquinolin-7-yl | 1,3-phenylene | Me | 41 | oil |
| 5ᵇ | 1,2-dihydro-1-methyl-2-oxoquinolin-6-yl | 5-fluoro-1,3-phenylene | Et | 61 | 110–112 |
| 6ᶜ | 1,2-dihydro-1-methyl-2-oxoquinolin-6-yl | 5-fluoro-1,3-phenylene | Me | 78 | 115–122 |
| 7ᵈ | 1,2-dihydro-1-ethyl-2-oxoquinolin-6-yl | 5-fluoro-1,3-phenylene | Me | 78 | oil |

Notes a. The product displayed the following characteristic NMR signals (CDCl₃, delta values) 1.19(d, 3H), 2.48(m, 2H), 3.16(s, 3H), 3.73(s, 3H), 3.74(m, 1H), 4.10(m, 2H), 5.21(s, 2H), 6.6–7.5(m, 9H).

b. The (2RS,3SR)-3-ethoxy-3-(5-fluoro-3-hydroxyphenyl)-2-methyltetrahydrofuran, used as a starting material, was obtained as follows:

A Grignard reagent was prepared by heating a mixture of 3-benzyloxy-5-fluorophenyl bromide (4.2 g), magnesium powder (0.365 g) and tetrahydrofuran (20 ml) to 40° C. for 1 hour. The reagent was cooled to ambient temperature and 2-methyltetrahydrofuran-3-one (1.16 ml) was added dropwise. The mixture was stirred at ambient temperature for 3 hours and then partitioned between ethyl acetate and water. The organic layer was washed with water, dried (MgSO₄) and evaporated. The residue was purified by column chromatography using a 19:1 v/v mixture of methylene chloride and diethyl ether as eluent. There was thus obtained (2RS,3SR)-3-(3-benzyloxy-5-fluorophenyl)-3-hydroxy-2-methyltetrahydrofuran (2.3 g, 64%), m.p. 83°–84° C.; the 2-methyl and 3-hydroxy groups being in a cis-relationship.

A portion (1.1 g) of the product so obtained was reacted with ethyl iodide using the procedure described in the second paragraph of Note b. below Table II in Example 6. There was thus obtained (2RS,3SR)-3-(3-benzyloxy-5-fluorophenyl)-3-ethoxy-2-methyltetrahydrofuran (0.82 g, 68%), as an oil.

A mixture of the product so obtained, 10% palladium-on-charcoal (0.1 g) and ethanol (5 ml) was stirred at ambient temperature under an atmosphere of hydrogen for 4 hours. The mixture was filtered and evaporated. There was thus obtained the required starting material (0.54 g, 92%), m.p. 136°–137° C.

c. The (2RS,3SR)-3-(5-fluoro-3-hydroxyphenyl)-3-methoxy-2-methyltetrahydrofuran, used as a starting material, was obtained as follows:

The procedures described in Note b. immediately above were repeated except that methyl iodide was used in place of ethyl iodide in the alkylation step. The required starting material was obtained in overall yield of 45%, m.p. 148°–152° C.

d. The product displayed the following characteristic NMR signals (CDCl₃, delta values) 1.21(d, 3H), 1.36(t, 3H), 2.5(m, 2H), 3.16(s, 3H), 3.7(q, 1H), 4.05(q, 2H), 4.4(q, 2H), 5.1(s, 2H), 6.5(m, 8H).

EXAMPLE 11

A mixture of 4-[3-(1,2-dihydro-1-methyl-2-oxoquinolin-6-ylmethoxy)phenyl]-4-hydroxytetrahydropyran (0.25 g), sodium hydride (60% w/w dispersion in mineral oil, 0.06 g) and dimethylformamide (20 ml) was stirred at ambient temperature for 30 minutes. Allyl bromide (1 ml) was added and the mixture was stirred at ambient temperature for 36 hours. The mixture was partitioned between ethyl acetate and a saturated aqueous ammonium chloride solution. The organic layer was washed with water, dried (MgSO₄) and evaporated. The residue was purified by column chromatography using a 4:1 v/v mixture of methylene chloride and diethyl ether as eluent. There was thus obtained 4-allyloxy-4-[3-(1,2-dihydro-1-methyl-2-oxoquinolin-6-ylmethoxy)phenyl]tetrahydropyran (0.17 g, 61%), as an oil.

NMR Spectrum: (CDCl₃, delta values) 2.0(m, 4H), 3.5–4.0(m, 6H), 3.72(s, 3H), 5.10(m, 1H), 5.12(s, 2H), 5.28(m, 1H), 5.76(m, 1H), 6.6–7.5(m, 9H).

The 4-[3-(1,2-dihydro-1-methyl-2-oxoquinolin-6-ylmethoxy)phenyl]-4-hydroxytetrahydropyran, used as a starting material, was obtained as follows:

Using the Grignard reaction procedure described in the portion of Example 1 which is concerned with the preparation of starting materials, 3-benzyloxybromobenzene was reacted with tetrahydropyran-4-one to give 4-(3-benzyloxyphenyl)-4-hydroxytetrahydropyran in 77% yield, m.p. 84°-86° C.

A mixture of the product so obtained (1 g), palladium-on-charcoal catalyst (0.1 g) and ethanol (10 ml) was stirred under two atmospheres of hydrogen for 6 hours. The mixture was filtered and the filtrate was evaporated. The residue was purified by column chromatography using a 50:50:1 v/v mixture of methylene chloride, diethyl ether and methanol as eluent. There was thus obtained 4-hydroxy-4-(3-hydroxyphenyl)tetrahydropyran (0.325 g, 48%), m.p. 165°-169° C.

Using the procedure described in Example 1, the product so obtained was reacted with 6-bromomethyl-1,2-dihydro-1-methylquinolin-2-one to give the required starting material in 70% yield, m.p. 165°-167° C.

EXAMPLE 12

Using the procedure described in Example 11, allyl bromide was reacted with the appropriate 4-hydroxytetrahydropyran to give the compounds described in the following table:

TABLE V

Q—CH$_2$—O—Ar    O—CH$_2$—CH=CH$_2$

| Ex. 12. Compd. No. | Q | Ar | Yield (%) | m.p. (°C.) |
|---|---|---|---|---|
| 1[a] | 1,2-dihydro-1-methyl-2-oxoquinolin-6-yl | 5-fluoro-1,3-phenylene | 51 | oil |
| 2[b] | 1,2-dihydro-1-methyl-2-oxoquinolin-6-yl | 5-trifluoromethyl-1,3-phenylene | 99 | oil |

Notes a. The product displayed the following characteristic NMR signals (CDCl$_3$, delta values) 1.85-2.10(m, 4H), 3.54-3.64(m, 2H), 3.73(s, 3H), 3.75-4.00(m, 4H), 5.10-5.25(m, 4H), 5.75-5.97(m, 1H), 6.63(m, 1H), 6.73-6.84(m, 3H), 7.37-7.43(m, 1H), 7.59-7.68(m, 3H).

The 4-[3-(1,2-dihydro-1-methyl-2-oxoquinolin-6-ylmethoxy)-5-fluorophenyl]-4-hydroxytetrahydropyran, used as a starting material, was obtained as follows:

Using the procedure described in the last paragraph of Note c. below Table I in Example 2, 4-(3-benzyloxy-5-fluorophenyl)-4-hydroxytetrahydropyran was hydrogenolysed to give 4-(5-fluoro-3-hydroxyphenyl)-4-hydroxytetrahydropyran in 79% yield, m.p. 158°-160° C.

Using the procedure described in Example 1, the product so obtained was reacted with 6-bromomethyl-1,2-dihydro-1-methylquinolin-2-one to give the required starting material in 72% yield, as a solid.

NMR Spectrum: (CDCl$_3$, delta values) 1.74(broad, 1H), 2.04-2.22(m, 4H), 3.73(s, 3H), 3.81-4.0(m, 4H), 5.10(s, 2H), 6.6(m, 1H), 6.73(d, 1H), 6.83(m, 1H), 6.95(t, 1H), 7.35-7.43(m, 1H), 7.54-7.70(m, 3H).

b. The product displayed the following characteristic NMR signals (CDCl$_3$, delta values) 1.9-2.1(m, 4H), 3.56-3.59(m, 2H), 3.73(s, 3H), 3.85-3.95(m, 4H), 5.0-5.3(m, 2H), 5.15(s, 2H), 5.1-5.31(m, 1H), 6.71-6.76(m, 1H), 7.1-7.69(m, 7H).

The 4-[3-(1,2-dihydro-1-methyl-2-oxoquinolin-6-ylmethoxy)-5-trifluoromethylphenyl]-4-hydroxytetrahydropyran, used as a starting material, was obtained as follows:

Using the procedure described in the last paragraph of Note s. below Table II in Example 6, 4-(3-benzyloxy-5-trifluoromethylphenyl)-4-hydroxytetrahydropyran was hydrogenolysed to give 4-hydroxy-4-(3-hydroxy-5-trifluoromethylphenyl)tetrahydropyran in 90% yield, as an oil.

Using the procedure described in Example 1, the product so obtained was reacted with 6-bromomethyl-1,2-dihydro-1-methylquinolin-2-one to give the required starting material in 70% yield.

NMR Spectrum: (CDCl$_3$, delta values) 1.64-1.69(d, 2H), 1.93(s, 1H), 2.09-2.25(m, 2H), 3.73(s, 3H), 3.88-3.99(m, 4H), 5.16(s, 2H), 6.7-6.75(d, 1H), 7.26-7.7(m, 6H).

EXAMPLE 13

A solution of 4-[5-fluoro-3-(2-propynyloxy)phenyl]-4-methoxytetrahydropyran (0.26 g) in acetonitrile (1.5 ml) was added to a mixture of 3-iodopyridine (0.21 g), bis(triphenylphosphine)palladium chloride (0.01 g), triethylamine (0.15 ml), cuprous iodide (0.01 g), and acetonitrile (1.5 ml) and the mixture was stirred and heated to 60° C. for 4 hours. The mixture was cooled to ambient temperature and partitioned between ethyl acetate and water. The organic phase was washed with water, dried (MgSO$_4$) and evaporated. The residue was purified by column chromatography using a 3:1 v/v mixture of hexane and ethyl acetate as eluent. There was thus obtained 4-[5-fluoro-3-(3-(3-pyridyl)prop-2-ynyloxy)phenyl]-4-methoxytetrahydropyran (0.25 g, 74%), m.p. 82°-83° C.

The 4-[5-fluoro-3-(2-propynyloxy)phenyl]-4-methoxytetrahydropyran used as a starting material was obtained as follows:

A mixture of 4-(5-fluoro-3-hydroxyphenyl)-4-methoxytetrahydropyran (5.34 g), propargyl bromide (80% w/v in toluene, 4.46 ml), potassium carbonate (5.52 g) and acetone (150 ml) was heated to reflux for 16 hours. The mixture was filtered and evaporated. The residue was partitioned between ethyl acetate and water. The organic phase was washed with water and with a saturated aqueous sodium chloride solution, dried (MgSO$_4$) and evaporated. The residue was purified by column chromatography using a 2:1 v/v mixture of ethyl acetate and hexane as eluent. There was thus obtained the required starting material (5.77 g, 91%), m.p. 71°-72° C.

EXAMPLE 14

The procedure described in Example 13 was repeated except that 3-chloro-2-iodopyridine was used in place of 3-iodopyridine. There was thus obtained 4-[3-(3-(3-chloropyrid-2-yl)prop-2-ynyloxy)-5-fluorophenyl]-4-methoxytetrahydropyran in 59% yield, m.p. 80°-82° C.

The 3-chloro-2-iodopyridine, used as a starting material, was obtained as follows:

A mixture of 2,3-dichloropyridine (0.74 g) and a saturated solution of sodium iodide in a mixture of methyl ethyl ketone (20 ml) and water (1 ml) was heated to reflux and aqueous hydroiodic solution (55% w/v, 0.5 ml) was added. The mixture was heated to reflux for 16 hours, cooled to ambient temperature, filtered and evaporated. The residue was dissolved in water (10 ml) and the solution was basified to pH 11 by the addition of pellets of sodium hydroxide. The basic solution was extracted with ethyl acetate. The organic phase was washed with water, dried (MgSO₄) and evaporated to give the required starting material, as an oil (0.66 g, 55%) which was used without further purification.

EXAMPLE 15

The procedure described in Example 13 was repeated except that 1-iodoisoquinoline (*Chem. Pharm. Bull. Jap.*, 1982, 30, 1731) was used in place of 3-iodopyridine. There was thus obtained 4-[5-fluoro-3-(3-(1-isoquinolyl)prop-2-ynyloxy)phenyl]-4-methoxytetrahydropyran in 67% yield, as an oil.

NMR Spectrum: (CDCl₃, delta values) 1.8–2.1(m, 4H), 2.9(s, 3H), 3.7–3.9(m, 4H), 5.1(s, 2H), 6.7–7.9(m, 7H), 8.25(d, 1H), 8.5(d, 1H).

EXAMPLE 16

Using the procedure described in Example 11, 4-[3-(1,2-dihydro-1-methyl-2-oxoquinolin-6-ylmethoxy)-5-trifluoromethylphenyl]-4-hydroxytetrahydropyran was reacted with methyl iodide to give 4-[3-(1,2-dihydro-1-methyl-2-oxoquinolin-6-ylmethoxy)-5-trifluoromethylphenyl]-4-methoxytetrahydropyran in 95% yield, m.p. 103° C.

EXAMPLE 17

Using the procedure described in Example 1,6-bromomethyl-1,2-dihydro-1-methylquinolin-2-one was reacted with (2RS,4RS)-4-(3-amino-5-hydroxyphenyl)-4-methoxy-2-methyltetrahydropyran to give (2RS,4RS)-4-[3-(1,2-dihydro-1-methyl-2-oxoquinolin-6-ylmethylamino)-5-hydroxyphenyl]-4-methoxy-2-methyltetrahydropyran in 46% yield, as an oil.

NMR Spectrum: (CD₃SOCD₃, delta values) 1.05(d, 3H), 1.1–2.4(m, 4H), 2.8(s, 3H), 3.0–3.5(m, 2H), 3.65(s, 3H), 3.6–3.9(m, 1H), 4.35(d, 2H), 5.95–6.3(m, 3H), 6.65(d, 1H), 7.4–7.75(m, 3H), 7.9(d, 1H), 8.9(m, 1H).

The (2RS,4RS)-4-(3-amino-5-hydroxyphenyl)-4-methoxy-2-methyltetrahydropyran, used as a starting material, was obtained as follows:

A mixture of (2RS,4RS)-4-(3-benzyloxy-5-nitrophenyl)-4-methoxy-2-methyltetrahydropyran (1 g), 5% palladium-on-charcoal catalyst (0.1 g), ethanol (10 ml) and methylene chloride (10 ml) was stirred under an atmosphere of hydrogen for 2 hours. The mixture was filtered and the filtrate was evaporated. The residue was purified by column chromatography using a 1:1 v/v mixture of toluene and ethyl acetate as eluent. There was thus obtained the required starting material (0.67 g, 99%), as an oil.

NMR Spectrum (CDCl₃, delta values) 1.2(d, 3H), 1.4–2.5(m, 4H), 2.95(s, 3H), 3.25–4.15(m, 6H), 6.0–6.5(m, 3H).

EXAMPLE 18

Using the procedure described in Example 1, 6-bromomethyl-1,2-dihydro-1-methylquinolin-2-one was reacted with (3RS,4SR)-3-hydroxy-4-(3-hydroxyphenyl)-4-methoxytetrahydropyran to give (3RS,4SR)-4-[3-(1,2-dihydro-1-methyl-2-oxoquinolin-6-ylmethoxy)phenyl]-3-hydroxy-4-methoxytetrahydropyran in 84% yield, m.p. 62°–66° C.

NMR Spectrum (CDCl₃, delta values) 1.85(m, 1H), 2.5(m, 1H), 2.96(s, 3H), 3.58(m, 1H), 3.72(s, 3H), 3.72–4.25(m, 4H), 5.13(s, 2H), 6.66–7.72(m, 9H).

The (3RS,4SR)-3-hydroxy-4-(3-hydroxyphenyl)-4-methoxytetrahydropyran, used as a starting material, was obtained as follows:

A mixture of 4-hydroxy-4-(3-benzyloxyphenyl)tetrahydropyran (12.5 g), 5-Angstrom molecular sieves (80 g) and toluene (90 ml) was heated to 80° C. for 9 hours. The mixture was filtered and the residue was washed in succession with toluene and acetone. The filtrate and washings were combined and evaporated. The residue was purified by column chromatography using methylene chloride as eluent. There was thus obtained 2,3-dihydro-4-(3-benzyloxyphenyl)-6H-pyran (10.5 g, 88%), as an oil.

m-Chloroperbenzoic acid (2.42 g) was added to a stirred suspension of a portion (2.5 g) of the product so obtained, sodium bicarbonate (1.18 g) and methylene chloride (30 ml) which had been cooled to 0° C., and the mixture was stirred at 0° C. for 1 hour and then at ambient temperature for 15 hours. The mixture was filtered and the residue was washed with methylene chloride. The combined filtrate and washings were washed with dilute aqueous sodium hydroxide solution, and with water, dried (MgSO₄) and evaporated. The epoxide (2.3 g, 90%) so obtained was used without further purification.

The procedure described in *Tet. Let.*, 1968, 24, 1755 was used to react the epoxide obtained above with sodium hydroxide. The product so obtained was purified by column chromatography using a 4:1 v/v mixture of methylene chloride and diethyl ether as eluent. There was thus obtained (3RS,4SR)-3,4-dihydroxy-4-(3-benzyloxyphenyl)tetrahydropyran (1.78 g, 73%) as an oil; the 3- and 4-hydroxy groups being in a trans-relationship.

A mixture of the product so obtained (1.76 g), imidazole (2 g), tert-butyldimethylsilyl chloride (2.26 g) and dimethylformamide (6 ml) was stirred at ambient temperature for 15 hours. The mixture was partitioned between diethyl ether and water. The organic layer was washed with water, dried (MgSO₄) and evaporated. The residue was purified by column chromatography using a 9:1 v/v mixture of methylene chloride and diethyl ether as eluent. There was thus obtained (3RS,4SR)-4-(3-benzyloxyphenyl)-3-(tert-butyldimethylsilyloxy)-4-hdyroxytetrahydropyran (1.9 g, 78%), m.p. 90°–92° C.

The product so obtained was methylated using the procedure described in the portion of Example 1 which is concerned with the preparation of starting materials. There was thus obtained (3RS,4SR)-4-(3-benzyloxyphenyl)-3-(tert-butyldimethylsilyloxy)-4-methoxytetrahydropyran (1.69 g, 89%), as an oil.

Tetra-n-butylammonium fluoride (1M in tetrahydrofuran; 16 ml) was added to a mixture of the compound so obtained and tetrahydrofuran (32 ml) and the mixture was stirred at ambient temperature for 15 hours. The mixture was evaporated and the residue was partitioned between diethyl ether and water. The organic phase was dried (MgSO₄) and evaporated. The residue was purified by column chromatography using a 9:1 v/v mixture of methylene chloride and diethyl ether as eluent. There was thus obtained (3RS,4SR)-4-methoxytetrahydropyran (1.06 g, 86%), m.p. 85°–86° C.

A mixture of the product so obtained, 10% palladium-on-charcoal catalyst (0.1 g) and ethanol (20 ml) was stirred at ambient temperature under an atmosphere of hydrogen for 15 hours. The mixture was filtered and evaporated and there was thus obtained the required starting material (0.7 g, 92%), m.p. 159°–160° C.

EXAMPLE 19

Using the methylation procedure described in the portion of Example 1 which is concerned with the preparation of starting materials, (3RS,4SR)-4-[3-(1,2-dihydro-1-methyl-2-oxoquinolin-6-ylmethoxy)phenyl]-3-hydroxy-4-methoxytetrahydropyran was reacted with methyl iodide in the presence of 15-crown-5 to give (3RS,4SR)-4-[3-(1,2-dihydro-1-methyl-2-oxoquinolin-6-ylmethoxy)phenyl]-3,4-dimethoxytetrahydropyran in 78% yield, as a glass.

NMR Spectrum (CDCl$_3$, delta values) 1.85(m, 1H), 2.5(m, 1H), 2.95(s, 6H), 3.07(m, 1H), 3.72(s, 3H), 3.72–3.94(m, 4H), 5.14(s, 2H), 6.66–7.5(m, 9H).

EXAMPLE 20

Using the procedure described in Example 1, 6-bromomethyl-1,2-dihydro-1-methylquinolin-2-one was reacted with (2S,4R)-4-(3-hydroxyphenyl)-4-methoxy-2-methyltetrahydropyran to give (2S,4R)-4-[3-(1,2-dihydro-1-methyl-2-oxoquinolin-6-ylmethoxy)phenyl]-4-methoxy-2-methyltetrahydropyran in 69% yield, m.p. 88°–90° C.

The (2S,4R)-4-(3-hydroxyphenyl)-4-methoxy-2-methyltetrahydropyran, used as a starting material, was obtained as follows:

A Grignard reagent was prepared by heating a mixture of 3-benzyloxybromobenzene (4.2 g), magnesium (0.4 g), and tetrahydrofuran (10 ml) to reflux for 30 minutes. The mixture was allowed to cool to approximately 40° C. and a solution of (2S)-2-methyltetrahydropyran-4-one (1.55 g) in tetrahydrofuran (7 ml) was added dropwise. The mixture was stirred and warmed to 40° C. for 3 hours. The mixture was partitioned between ethyl acetate and cold dilute aqueous hydrochloric acid solution. The organic phase was washed with a saturated aqueous sodium chloride solution, dried (MgSO$_4$) and evaporated. The residue was purified by column chromatography using a 10:3 v/v mixture of toluene and ethyl acetate as eluent. There was thus obtained, as a mixture of diastereoisomers, (2S,4R)- and (2S,4S)-4-(3-benzyloxyphenyl)-4-hydroxy-2-methyltetrahydropyran (3.71 g, 92%), as an oil, which was partly separated to give a fraction (2.33 g) which was enriched in the less polar diastereoisomer.

Sodium hydride (55% w/w dispersion in mineral oil, 0.39 g) was added to a solution of the enriched fraction so obtained (2.33 g) in dimethylformamide (16 ml) which had been cooled to −5° C. and the mixture was stirred at this temperature for 1 hour. Methyl iodide (0.61 ml) was added and the mixture was stirred for 2 hours and allowed to warm to ambient temperature. The mixture was partitioned between ethyl acetate and ice-cold water. The organic phase was washed with a saturated aqueous sodium chloride solution, dried (MgSO$_4$) and evaporated. The residue was purified by column chromatography using a 20:1 v/v mixture of toluene and ethyl acetate as eluent. There was thus obtained (2S,4R)-4-(3-benzyloxyphenyl)-4-methoxy-2-methyltetrahydropyran (1.99 g, 82%), as an oil.

NMR Spectrum: (CDCl$_3$, delta values) 1.2(d, 3H), 1.5–1.65(m, 1H), 1.9–2.05(m, 3H), 2.96(s, 3H), 3.8–4.0(m, 3H), 5.1(s, 2H), 6.85–7.05(m, 3H), 7.2–7.5(m, 6H).

A mixture of the product so obtained (1.62 g), 10% palladium-on-charcoal catalyst (0.28 g) and isopropanol (50 ml) was stirred under an atmosphere of hydrogen for 5 hours. The mixture was filtered and the filtrate was evaporated. There was thus obtained the required starting material in quantitative yield, as an oil.

The (2S)-2-methyltetrahydropyran-4-one, used as a starting material above, was obtained as follows:

Sodium bis-(2-methyoxyethoxy)aluminium hydride (3.4M in toluene, 200 ml) was added over a period of 30 minutes to a solution of (−)-(2S,3S,4S)-2,3-epoxyhept-6-en-4-ol (29 g; *J. Org. Chem.*, 1983, 48, 5093, compound No. (−)14 therein) in tetrahydrofuran (1100 ml) which had been cooled to −15° C. and the mixture was stirred for 16 hours and allowed to warm to ambient temperature. The mixture was cooled in an ice-bath and dilute aqueous sulphuric acid (10% w/v, 1350 ml) was added slowly. Sodium chloride was added to produce two phases. The organic phase was separated and the aqueous phase was extracted with ethyl acetate. The combined organic phases were washed with a saturated aqueous sodium chloride solution, dried (MgSO$_4$) and evaporated. The residue was purified by column chromatography using a 2:3 v/v mixture of hexane and ethyl acetate as eluent. There was thus obtained (2S,4S)-hept-6-ene-2,4-diol (20 g, 67%), as an oil.

NMR Spectrum: (CDCl$_3$, delta values) 1.23(d, 3H), 1.63(t, 2H), 2.18–2.4(m, 4H), 3.93–4.38(m, 2H), 5.08–5.25(m, 2H), 5.70–5.96(m, 1H).

A solution of a portion (5.6 g) of the product so obtained in methanol (875 ml) was cooled to −20° C. and a stream of ozone-containing oxygen (approximately 5% ozone) was bubbled into the solution for 130 minutes. Oxygen gas and then argon were bubbled into the solution to remove any excess ozone. Dimethyl sulphide (20 ml) was added and the mixture was allowed to warm to ambient temperature. The mixture was evaporated and the residue was purified by column chromatography using ethyl acetate as eluent. There was thus obtained as a mixture of diastereoisomers (2S,4R,6R)- and (2S,4R,6S)-4,6-dihydroxy-2-methyltetrahydropyran (3.7 g, 67%), as an oil.

After repetition of the above steps, a saturated solution of hdyrogen chloride in ethanol (90 drops) was added to a solution of the product so obtained (19 g) in ethanol (90 ml) which had been cooled in an ice-bath and the mixture was stored at 5° C. for 16 hours. The mixture was evaporated to give as a mixture of diastereoisomers (2S,4R,6R)- and (2S,4R,6S)-6-ethoxy-4-hydroxy-2-methyltetrahydropyran in quantitative yield, as an oil, which was used without further purification.

A solution of the product so obtained in dimethylformamide (45 ml) was cooled to 0° C. and there were added in turn imidazole (20.4 g) and molecular sieve (4 Angstrom, 5 g). Triethylsilyl chloride (24.3 ml) was added dropwise and the mixture was stirred at 0° C. for 2 hours. The mixture was poured onto ice and an ethyl acetate extract was taken. The organic phase was dried (MgSO$_4$) and evaporated. The residue was dissolved in ether (300 ml) and the solution was washed with cold water. The organic layer was separated, dried (MgSO$_4$) and evaporated to give as a mixture of diastereoisomers (2S,4R,6R)- and (2S,4R,6S)-6-ethoxy-2-methyl-4-triethylsilyloxytetrahydropyran (36 g, 91%), which was used without further purification.

Triethylsilane (15.7 g) and trimethylsilyl trifluoromethanesulphonate (29.1 g) were added in turn to a solution of the product so obtained in methylene chloride (300 ml) which had been cooled to 5° C. and the mixture was stirred at 5° C. for 30 minutes. The mixture was poured into ice-cold water (50 ml) and the resultant mixture was stirred for 5 minutes. The mixture was neutralised by the portionwise addition of sodium bicarbonate. The organic layer was separated and the aqueous layer was saturated with sodium chloride and extracted with ethyl acetate. The organic solutions were combined, dried (MgSO4) and evaporated. The residue was purified by column chromatography using a 4:1 v/v mixture of hexane and ethyl acetate as eluent. There was thus obtained (2S,4S)-4-hydroxy-2-methyltetrahydropyran (6.2 g, 41%).

NMR Spectrum (CDCl3, delta values) 1.15-1.25(m, 4H), 1.4-1.6(m, 1H), 1.8-2.0(m, 2H), 3.3-3.5(m, 2H), 3.7-3.8(m, 1H), 4.0(m, 1H).

Jones reagent (*J. Chem. Soc*, 1951, 2407; 13.3 ml of a 8M solution of chromium trioxide in aqueous sulphuric acid) was added dropwise to a solution of the product so obtained in acetone (250 ml) which was cooled to 5° C. Isopropanol (approximately 20 drops) was added to destroy the excess of oxidant and the mixture was stirred at ambient temperature for 30 minutes. The mixture was filtered and the filtrate was evaporated. The residue was dissolved in diethyl ether (10 ml) and the solution was filtered through Kieselgel 60H silica and evaporated. There was thus obtained (2S)-2-methyltetrahydropyran-4-one (4.85 g, 81%), as an oil.

NMR Spectrum: (CDCl3, delta values) 1.3(d, 3H), 2.2-2.7(m, 4H), 3.6-3.8(m, 2H), 4.2-4.3(m, 1H).

EXAMPLE 21

Using the procedure described in Example 1, 6-bromomethyl-1,2-dihydro-1-methylquinolin-2-one was reacted with (2S,4R)-4-(5-fluoro-3-hydroxyphenyl)-4-methoxy-2-methyltetrahydropyran to give (2S,4R)-4-[5-fluoro-3-(1,2-dihydro-1-methyl-2-oxoquinolin-6-ylmethoxy)phenyl]-4-methoxy-2-methyltetrahydropyran in 66% yield, m.p. 91°-93° C.

The (2S,4R)-4-(5-fluoro-3-hydroxyphenyl)-4-methoxy-2-methyltetrahydropyran, used as a starting material, was obtained as follows:

The procedures described in the portion of Example 20 which is concerned with the preparation of starting materials were repeated except that 3-benzyloxy-1-bromo-5-fluorobenzene was used in place of 3-benzyloxybromobenzene. There were thus obtained in turn: as a mixture of diastereoisomers (2S,4R)- and (2S,4S)-4-(3-benzyloxy-5-fluorophenyl)-4-hydroxy-2-methyltetrahydropyran in 87% yield, as an oil; (2S,4R)-4-(3-benzyloxy-5-fluorophenyl)-4-methoxy-2-methyltetrahydropyran in 58% yield, as an oil, NMR Spectrum: (CDCl3, delta values) 1.2(d, 3H), 1.5-1.6(m, 1H), 1.8-2.0(m, 3H), 3.0(s, 3H), 3.8-4.0(m, 3H), 5.05(s, 2H), 6.6-6.8(m, 3H), 7.3-7.5(m, 5H); and the required starting material in quantitative yield, as an oil; NMR Spectrum data, obtained after the chiral shift reagent (−)-1-(9-anthranyl)-2,2,2-trifluoroethanol had been added, showed that the product was 98.6% optically pure.

EXAMPLE 22

Using the procedure described in Example 1, 6-bromomethyl-1,2-dihydro-1-methylquinolin-2-one was reacted with 4-(4-hydroxy-3-methoxyphenyl)-4-methoxytetrahydropyran to give 4-[4-(1,2-dihydro-1-methyl-2-oxoquinolin-6-ylmethoxy)-3-methoxyphenyl]-4-methoxytetrahydropyran in 49% yield, m.p. 172°-173° C. (recrystallised from ethyl acetate).

The 4-(4-hydroxy-3-methoxyphenyl)-4-methoxytetrahydropyran, used as a starting material, was obtained as follows:

Using the procedure described in Example 1, 2-bromomethylnaphthalene was reacted with 4-bromo-2-methoxyphenol to give 3-methoxy-4-(naphth-2-ylmethoxy)bromobenzene in 62% yield, m.p. 108° C.

Using the procedure described in the second paragraph of Note c. below Table I in Example 2, the product so obtained was reacted with tetrahydropyran-4-one to give 4-hydroxy-4-[3-methoxy-4-(naphth-2-ylmethoxy)phenyl]tetrahydropyran in 44% yield, m.p. 150°-151° C. (recrystallised from ethyl acetate).

Using the procedure described in the penultimate paragraph of Note s. below Table II in Example 6, the product so obtained was reacted with methyl iodide to give 4-methoxy-4-[3-methoxy-4-(naphth-2-ylmethoxy)phenyl]tetrahydropyran in 52% yield, m.p. 129° C. (recrystallised from ethyl acetate).

A mixture of the product so obtained (0.241 g), 10% palladium-on-charcoal catalyst (0.02 g) and ethanol (25 ml) was stirred under an atmosphere of hydrogen for 90 minutes. The mixture was filtered and the filtrate was evaporated. The residue was purified by column chromatography using increasingly polar mixtures of hexane and ethyl acetate as eluent. There was thus obtained the required starting material (0.142 g, 94%) m.p. 92°-93° C.

EXAMPLE 23

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
| --- | --- |
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
| --- | --- |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
| --- | --- |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
| --- | --- |
| Compound X | 10 mg |
| Lactose Ph.Eur | 488.5 |
| Magnesium stearate | 1.5 |

| (e) Injection I | (50 mg/ml) |
| --- | --- |
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
| --- | --- |
| Compound X | 1.0% w/v |
| Sodium phosphate BP | 3.6% w/v |
| 0.1M Sodium hydroxide solution | 15.0% v/v |
| Water for injection to 100% | |

(1 mg/ml,

|     |                          |                 |
| --- | ------------------------ | --------------- |
| (g) | Injection III            | buffered to pH6)|
|     | Compound X               | 0.1% w/v        |
|     | Sodium phosphate BP      | 2.26% w/v       |
|     | Citric acid              | 0.38% w/v       |
|     | Polyethylene glycol 400  | 3.5% w/v        |
|     | Water for injection to 100% |              |
| (h) | Aerosol I                | mg/ml           |
|     | Compound X               | 10.0            |
|     | Sorbitan trioleate       | 13.5            |
|     | Trichlorofluoromethane   | 910.0           |
|     | Dichlorodifluoromethane  | 490.0           |
| (i) | Aerosol II               | mg/ml           |
|     | Compound X               | 0.2             |
|     | Sorbitan trioleate       | 0.27            |
|     | Trichlorofluoromethane   | 70.0            |
|     | Dichlorodifluoromethane  | 280.0           |
|     | Dichlorotetrafluoroethane| 1094.0          |
| (j) | Aerosol III              | mg/ml           |
|     | Compound X               | 2.5             |
|     | Sorbitan trioleate       | 3.38            |
|     | Trichlorofluoromethane   | 67.5            |
|     | Dichlorodifluoromethane  | 1086.0          |
|     | Dichlorotetrafluoroethane| 191.6           |
| (k) | Aerosol IV               | mg/ml           |
|     | Compound X               | 2.5             |
|     | Soya lecithin            | 2.7             |
|     | Trichlorofluoromethane   | 67.5            |
|     | Dichlorodifluoromethane  | 1086.0          |
|     | Dichlorotetrafluoroethane| 191.6           |

Note

The above formulations may be obtained by conventional procedures well known in the pharmaceutical art. The tablets (a)-(c) may be enteric coated by conventional means, for example to provide a coating of cellulose acetate phthalate. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE

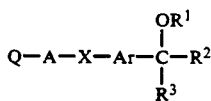   I

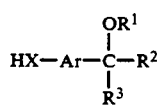   II

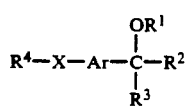   III

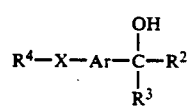   IV

-continued
CHEMICAL FORMULAE

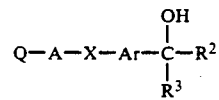   V

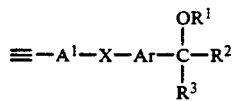   VI

What we claim is:
1. A heterocycle of the formula I

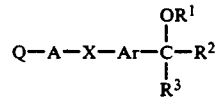   I wherein
Q is 2-oxoquinolinyl which may optionally bear one or two substituents selected from halogeno, (1-4C)alkyl, (1-4C)alkoxy, fluoro-(1-4C)alkyl, amino-(1-4C)alkyl, (1-4C)alkylamino-(1-4C)alkyl, di-[(1-4C)alkyl]amino-(1-4C)alkyl and phenyl-(1-4C)alkyl, and wherein the phenyl group in said phenyl-(1-4C)alkyl substituent may optionally bear a substituent selected from halogeno, (1-4C)alkyl and (1-4C)alkoxy;
wherein A is (1-6C)alkylene;
wherein X is oxy, thio or imino;
wherein Ar is phenylene which may optionally bear one or two substituents selected from halogeno, hydroxy, amino, ureido, (1-4C)alkyl, (1-4C)alkoxy, fluoro-(1-4C)alkyl and cyano-(1-4C)alkoxy;
wherein $R^1$ is hydrogen, (1-6C)alkyl, (3-6C)alkenyl or (3-6C)alkynyl; and wherein $R^2$ and $R^3$ together form a group of the formula $—A^2—X^2—A^3—$ which, together with the carbon atom to which $A^2$ and $A^3$ are attached, defines a ring having 5 or 6 ring atoms, wherein $A^2$ and $A^3$, which may be the same or different, each is (1-3C)alkylene and $X^2$ is oxy, and which ring may bear one or two substituents, which may be the same or different, selected from hydroxy, (1-4C)alkyl and (1-4C)alkoxy; or a pharmaceutically-acceptable salt thereof.

2. A heterocycle of the formula I as claimed in claim 1 wherein
Q is 2-oxoquinolinyl which may optionally bear one or two substituents selected from fluoro, chloro, hydroxy, methyl, ethyl, propyl, trifluoromethyl, 2-fluoroethyl, 2-dimethylaminoethyl and benzyl;
wherein A is methylene;
wherein X is oxy or imino;
wherein Ar is 1,3-phenylene or 1,4-phenylene which may optionally bear one or two substituents selected from fluoro, chloro, hydroxy, amino, ureido, methyl, methoxy, dimethylamino, trifluoromethyl and cyanomethoxy;
wherein $R^1$ is methyl, ethyl, allyl or 2-propynyl; and wherein $R^2$ and $R^3$ together form a group of the formula $—A^2—X^2—A^3—$ which, together with the carbon atom to which $A^2$ and $A^3$ are attached defines a ring having 5 or 6 ring atoms, wherein $A^2$ and $A^3$ which may be the same or different, each is methylene, ethylene or trimethylene and $X^2$ is oxy, and which ring may bear one or two substituents selected from hydroxy, methyl, ethyl and methoxy; or a pharmaceutically-acceptable salt thereof.

3. A heterocycle of the formula I as claimed in claim 1 wherein

Q is 1,2-dihydro-2-oxoquinolin-3-yl, 1,2-dihydro-2-oxoquinolin-6-yl or 1,2-dihydro-2-oxoquinolin-7-yl which may optionally bear one or two substituents selected from fluoro, chloro, methyl, methoxy and trifluoromethyl;

A is methylene;

X is oxy;

Ar is 1,3-phenylene or 1,4-phenylene which may optionally bear one substituent selected from fluoro, chloro, hydroxy, amino, methyl, methoxy, trifluoromethyl and cyanomethoxy;

$R^1$ is methyl, ethyl, allyl or 2-propynyl; and $R^2$ and $R^3$ together form a group of the formula $-A^2-X^2-A^3-$ which, together with the carbon atom to which $A^2$ and $A^3$ are attached, defines a ring having 5 or 6 ring atoms, wherein $A^2$ and $A^3$, which may be the same or different, each is methylene, ethylene or trimethylene and $X^2$ is oxy, and which ring may bear a substituent selected from hydroxy, methyl, methoxy and ethoxy;

or a pharmaceutically-acceptable salt thereof.

4. A heterocycle of the formula I as claimed in claim 1 wherein

Q is 1,2-dihydro-2-oxoquinolin-3-yl, 1,2-dihydro-2-oxoquinolin-5-yl, 1,2-dihydro-2-oxoquinolin-6-yl or 1,2-dihydro-2-oxoquinolin-7-yl which may optionally bear one or two substituents selected from fluoro, methyl, ethyl, 2-fluoroethyl, 2-dimethylaminoethyl and benzyl;

wherein A is methylene;

wherein X is oxy or imino;

wherein Ar is 1,3-phenylene or 1,4-phenylene which may optionally bear one or two substituents selected from fluoro, hydroxy, amino, ureido, methoxy, trifluoromethyl and cyanomethoxy;

wherein $R^1$ is methyl, ethyl or allyl; and wherein $R^2$ and $R^3$ together form a group of the formula $-A^2-X^2-A^3-$ which, together with the carbon atom to which $A^2$ and $A^3$ are attached defines a ring having 5 or 6 ring atoms, wherein $A^2$ is ethylene, $A^3$ is methylene or ethylene and $X^2$ is oxy, and which ring may bear one or two substituents selected from hydroxy, methyl and methoxy;

or a pharmaceutically-acceptable salt thereof.

5. A heterocycle of the formula I as claimed in claim 1 wherein

Q is 1,2-dihydro-2-oxoquinolin-3-yl, 1,2-dihydro-2-oxoquinolin-5-yl, 1,2-dihydro-2-oxoquinolin-6-yl or 1,2-dihydro-2-oxoquinolin-7-yl which may optionally bear one or two substituents selected from fluoro, methyl, ethyl, 2-fluoroethyl, 2-dimethylaminoethyl and benzyl;

wherein A is methylene;

wherein X is oxy;

wherein Ar is 1,3-phenylene or 1,4-phenylene which may optionally bear one or two substituents selected from fluoro, amino, ureido, methoxy and trifluoromethyl;

wherein $R^1$ is methyl, ethyl or allyl; and wherein $R^2$ and $R^3$ together from a group of the formula $-A^2-X^2-A^3-$ which, together with the carbon atom to which $A^2$ and $A^3$ are attached defines a ring having 5 or 6 ring atoms, wherein $A^2$ is ethylene, $A^3$ is methylene or ethylene and $X^2$ is oxy, and which ring may bear one or two substituents selected from hydroxy, methyl and methoxy;

or a pharmaceutically-acceptable salt thereof.

6. A heterocycle of the formula I as claimed in claim 1 wherein

Q is 1,2-dihydro-2-oxoquinolin-3-yl or 1,2-dihydro-2-oxoquinolin-6-yl which bears a 1-substituent selected from methyl, ethyl, 2-fluoroethyl and benzyl;

wherein A is methylene;

wherein X is oxy;

wherein Ar is 1,3-phenylene which may optionally bear one or two substituents selected from fluoro, amino and trifluoromethyl;

wherein $R^1$ is methyl, ethyl or allyl; and wherein $R^2$ and $R^3$ together form a group of the formula $-A^2-X^2-A^3-$ which, together with the carbon atom to which $A^2$ and $A^3$ are attached defines a ring having 5 or 6 ring atoms, wherein $A^2$ is ethylene, $A^3$ is methylene or ethylene and $X^2$ is oxy, and which ring may bear a methyl substituent alpha to $X^2$;

or a pharmaceutically-acceptable salt thereof.

7. A heterocycle of the formula I as claimed in claim 1 selected from the group consisting of:

4-[3-(1,2-dihydro-1-methyl-2-oxoquinolin-3-ylmethoxy)phenyl]-4-methoxytetrahydropyran, 4-[3-(1,2-dihydro-1-methyl-2-oxoquinolin-6-ylmethoxy)phenyl]-4-methoxytetrahydropyran, 4-[5-fluoro-3-(1,2-dihydro-1-methyl-2-oxoquinolin-6-ylmethoxy)phenyl]-4-methoxytetrahydropyran, 4-allyloxy-4-[5-fluoro-3-(1,2-dihydro-1-methyl-2-oxoquinolin-6-ylmethoxy)phenyl]tetrahydropyran, 4-[5-fluoro-3-(1,2-dihydro-1-(2-fluoroethyl)-2-oxoquinolin-6-ylmethoxy)phenyl]-4-methoxytetrahydropyran, 4-[2,5-difluoro-3-(1,2-dihydro-1-methyl-2-oxoquinolin-6-ylmethoxy)phenyl]-4-methoxytetrahydropyran, 4-[3-(1,2-dihydro-1-methyl-2-oxoquinolin-6-ylmethoxy)-5-trifluoromethylphenyl]-4-methoxytetrahydropyran, 4-allyloxy-4-[3-(1,2-dihydro-1-methyl-2-oxoquinolin-6-ylmethoxy)-5-trifluoromethylphenyl]tetrahydropyran, (2RS,4SR)-4-[5-fluoro-3-(1,2-dihydro-1-methyl-2-oxoquinolin-6-ylmethoxy)phenyl]-4-methoxy-2-methyltetrahydropyran, (2RS,4SR)-4-[5-fluoro-3-(1,2-dihydro-1-ethyl-2-oxoquinolin-6-ylmethoxy)phenyl]-4-methoxy-2-methyltetrahydropyran, (2RS,4SR)-4-[5-amino-3-(1,2-dihydro-1-methyl-2-oxoquinolin-6-ylmethoxy)phenyl]-4-methoxy-2-methyltetrahydropyran, (2S,4R)-4-[3-(1,2-dihydro-1-methyl-2-oxoquinolin-6-ylmethoxy)phenyl]-4-methoxy-2-methyltetrahydropyran, (2S,4R)-4-[5-fluoro-3-(1,2-dihydro-1-methyl-2-oxoquinolin-6-ylmethoxy)phenyl]-4-methoxy-2-methyltetrahydropyran and (2RS,3SR)-3-[5-fluoro-3-(1,2-dihydro-1-ethyl-2-oxoquinolin-6-ylmethoxy)phenyl]-3-methoxy-2-methyltetrahydrofuran;

or a pharmaceutically-acceptable salt thereof.

8. The heterocycle of the formula I as claimed in claim 1 wherein said heterocycle is 4-[5-fluoro-3-(1,2-dihydro-1-methyl-2-oxoquinolin-6-ylmethoxy)phenyl]-4-methoxytetrahydropyran 9. A heterocycle of the formula I

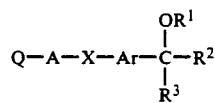

wherein Q is quinolyl;
wherein A is (1-6C)alkylene;
wherein X is oxy;
wherein Ar is phenylene which may optionally bear one or two substituents selected from halogeno, amino, (1-4C)alkyl, (1-4C)alkoxy and fluoro-(1-4C)alkyl;
wherein $R^1$ is (1-6C)alkyl, (3-6C)alkenyl or (3-6C)alkynyl; and wherein
$R^2$ and $R^3$ together form a group of the formula $-A^2-X^2-A^3-$ which, together with the carbon atom to which $A^2$ and $A^3$ are attached, defines a ring having 5 or 6 ring atoms, wherein $A^2$ and $A^3$, which may be the same or different, each is (1-3C)alkylene and $X^2$ is oxy, and which ring may bear one or two substituents, which may be the same or different, selected from hydroxy, (1-4C)alkyl and (1-4C)alkoxy;
or a pharmaceutically-acceptable salt thereof.

10. A heterocycle of the formula I as claimed in claim 9 wherein
Q is quinolyl;
wherein A is methylene;
wherein X is oxy;
wherein Ar is 1,3-phenylene or 1,4-phenylene which may optionally bear one or two substituents selected from fluoro, chloro, amino, methyl, methoxy and trifluoromethyl;
wherein $R^1$ is methyl, ethyl, allyl or 2-propynyl; and
wherein $R^2$ and $R^3$ together form a group of the formula $-A^2-X^2-A^3-$ which, together with the carbon atom to which $A^2$ and $A^3$ are attached defines a ring having 5 or 6 ring atoms, wherein $A^2$ and $A^3$ which may be the same or different, each is methylene, ethylene or trimethylene and $X^2$ is oxy, and which ring may bear one or two substituents selected from hydroxy, methyl, ethyl and methoxy;
or a pharmaceutically-acceptable salt thereof.

11. A heterocycle of the formula I as claimed in claim 9 wherein
Q is 2-quinolyl, 3-quinolyl or 6-quinolyl;
A is methylene;
X is oxy;
Ar is 1,3-phenylene which may optionally bear one substituent selected from fluoro, chloro and trifluoromethyl;
$R^1$ is methyl, ethyl or allyl; and
$R^2$ and $R^3$ together form a group of the formula $-A^2-X^2-A^3-$ which, together with the carbon atom to which $A^2$ and $A^3$ are attached, defines a ring having 6 ring atoms, wherein each of $A^2$ and $A^3$ is ethylene and
$X^2$ is oxy, and which ring may bear one methyl substituent; or a pharmaceutically-acceptable salt thereof.

12. A heterocycle of the formula I as claimed in claim 9 wherein
Q is 6-quinolyl;
wherein A is methylene;
wherein X is oxy;
wherein Ar is 1,3-phenylene which may optionally bear one fluoro substituent;
wherein $R^1$ is methyl; and
wherein $R^2$ and $R^3$ together form a group of the formula $-A^2-X^2-A^3-$ which, together with the carbon atom to which $A^2$ and $A^3$ are attached defines a ring having 6 ring atoms, wherein $A^2$ is ethylene, $A^3$ is ethylene and $X^2$ is oxy;
or a pharmaceutically-acceptable salt thereof.

13. A heterocycle of the formula I as claimed in claim 9 being:
4-[5-fluoro-3-(6-quinolylmethoxy)phenyl]-4-methoxytetrahydropyran.

14. A pharmaceutical composition which comprises a heterocycle of the formula I, or a pharmaceutically-acceptable salt thereof, as claimed in claim 1 or 9 in association with a pharmaceutically-acceptable diluent or carrier.

15. A method of treating a disease or medical condition mediated alone or in part by one or more leukotrienes which comprises administering to a warm-blooded animal requiring such treatment an effective amount of a heterocycle of the formula I, or a pharmaceutically-acceptable salt thereof, as claimed in claim 1 or 9.

* * * * *